(12) United States Patent
Croteau et al.

(10) Patent No.: US 6,420,159 B2
(45) Date of Patent: Jul. 16, 2002

(54) 1-DEOXY-D-XYLULOSE-5-PHOSPHATE REDUCTOISOMERASES, AND METHODS OF USE

(75) Inventors: Rodney B. Croteau; Bernd M. Lange, both of Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/874,562

(22) Filed: Jun. 4, 2001

Related U.S. Application Data

(62) Division of application No. 09/491,362, filed on Jan. 26, 2000, now Pat. No. 6,281,017.
(60) Provisional application No. 60/118,349, filed on Feb. 3, 1999.

(51) Int. Cl.[7] .............................. C12N 9/90; C12N 9/02
(52) U.S. Cl. ...................................................... 435/233
(58) Field of Search ................................ 435/233, 189

(56) References Cited

PUBLICATIONS

Takahashi, S. et al. "A 1–deoxy–D–xylulose–5–phosphate reductoisomerase catalyzing the formation of 2–C–methyl–D–erythritol–4–phosphate in an alternative nonmevalonate pathway for terpenoid biosynthesis," *Proc. Natl. Acad. Sci. USA*, 95:9879–9884 (1998).
GenBank Accession No. D64000, intially released on Jun. 28, 1996. Discloses the nucleic acid sequence of the Synechocystis genome that includes a nucleic acid sequence that encodes a putative 1–deoxy–D–xylulose–5–phosphate reductoisomerase (the amino acid sequence of which is highlighted in yellow).
GenBank Accession No. B69881, intially released on Nov. 26, 1997. Discloses amino acid sequence of a putative 1–deoxy–D–xylulose–5–phosphate reductoisomerase from *Bacillus subtilis*.
GenBank Accession No. U32763, initially released on Jul. 25, 1995. Discloses nucleic acid sequence of a portion of the *Haemophilus influenzae* genome that includes nucleic acid sequence that encodes a putative 1–deoxy–D–xylulose–5–phosphate reductoisomerase (the amino acid sequence of which is highlighted in yellow).
GenBank Accession No. CAA98375, initially released on Jun. 11, 1998. Discloses amino acid sequence of a putative 1–deoxy–D–xylulose–5–phosphate reductoisomerase encoded within the *Mycobacterium tuberculosis* genome.
GenBank Accession No. AE000541, initially released on Aug. 6, 1997. Discloses the nucleic acid sequence of a portion of the *Helicobacter pylori* genome that includes a nucleic acid sequence that encodes a putative 1–deoxy–D–xylulose–5–phosphate reductoisomerase (the amino acid sequence of which is highlighted in yellow).

GenBank Accession No. T43949, initially released on Jan. 25, 1995. Discloses the nucleic acid sequence of a truncated Arabidopsis cDNA fragment of unknown function (disclosed in the present application as SEQ ID NO: 10) that shows homology to the peppermint cDNA molecule set forth in the present application as SEQ ID NO: 2.

GenBank Accession No. AB009053, initially released on Nov. 27, 1997. Discloses the nucleic acid sequence of chromosome 5 of *Arabidopsis thaliana*. The disclosed genomic sequence includes as Arabidopsis gene of unknown function (disclosed in the present application as SEQ ID NO: 11) that shows homology to the peppermint cDNA set forth in the present application as SEQ ID NO: 2.

Kuzuyama, T. et al. "Direct Formation of 2–C–Methyl–D–Erythritol 4–Phosphate from 1–Deoxy–D–Xylulose 5 Phosphate by 1 Deoxy–D–Xylulose –5–Phosphate Reductoisomerase, a New Enzyme in the Non–Mevalonate Pathway to Isopentenyl Disphosphate," *Tetrahedron Letters*, 39:4509–4512 (1998).

Kuzuyama, T. et al. "Fosmidomycin, a Specific Inhibitor of 1–Deoxy–D–Xylulose 5 Phosphate Reductoisomerase in the Nonmevalonate Pathway for Terponoid Biosynthesis," *Tetrahedron Letters*, 39:7913–7916 (1998).

Schwender, J. et al. *FEBS Lett*, 455:140–144 (1999).

Lange, B.M. et al. *Arch. Biochem Biophys*, 365(1):170–174 (1999).

Bolton, E.T. et al., "A General Method for the Isolation of RNA Complementary to DNA," *Proc. N.A.S.*, 48:1390 (1962).

Bonner, T.I. et al., "Reduction in the Rate of DNA Reassociation by Sequence Divergence," *Mol. Biol.*, 81:123–135 (1973).

*Primary Examiner*—Charles L. Patterson, Jr.
(74) *Attorney, Agent, or Firm*—Christensen O'Connor Johnson Kindness PLLC

(57) ABSTRACT

The present invention relates to isolated DNA sequences which code for the expression of plant 1-deoxy-D-xylulose-5-phosphate reductoisomerase protein, such as the sequence presented in SEQ ID NO:1 which encodes a 1-deoxy-D-xylulose-5-phosphate reductoisomerase protein from peppermint (*Mentha x piperita*). Additionally, the present invention relates to isolated plant 1-deoxy-D-xylulose-5-phosphate reductoisomerase protein. In other aspects, the present invention is directed to replicable recombinant cloning vehicles comprising a nucleic acid sequence which codes for a plant 1-deoxy-D-xylulose-5-phosphate reductoisomerase, to modified host cells transformed, transfected, infected and/or injected with a recombinant cloning vehicle and/or DNA sequence of the invention.

4 Claims, 3 Drawing Sheets

US 6,420,159 B2

1-DEOXY-D-XYLULOSE-5-PHOSPHATE REDUCTOISOMERASES, AND METHODS OF USE

RELATED APPLICATIONS

The present application is a divisional of prior U.S. application Ser. No. 09/491,362, filed Jan. 26, 2000 now U.S. Pat. No. 6,281,017, priority from the filing date of which is hereby claimed under 35 U.S.C. §120, and further claims benefit of priority from U.S. Provisional Application Serial No. 60/118,349, filed on Feb. 3, 1999, the benefit of which is hereby claimed under 35 U.S.C. §119. The entire disclosure of the prior applications, from which priority is claimed, is considered as being part of the disclosure of this application and is hereby incorporated by reference herein.

GOVERNMENT RIGHTS

This invention was funded in part by grant number DE-FG00-96ER20212, from the U.S. Department of Energy. The government has certain rights in the invention.

FIELD OF THE INVENTION

This invention relates to nucleic acid sequences encoding 1-deoxy-D-xylulose-5-phosphate reductoisomerase.

BACKGROUND OF THE INVENTION

Isoprenoids are a large and structurally diverse group of compounds that play essential roles in plants as hormones, photosynthetic pigments, electron carriers, and components of membranes, and that also serve in communication and defense (Harborne, J. B. (1991) in Ecological Chemistry and Biochemistry of Plant Terpenoids (Harborne, J. B., and Tomas-Barberan, R. A., Eds.), pp. 399–426. Clarendon Press, Oxford). Until recently, it was widely accepted that all isoprenoids were synthesized via the acetate/mevalonate pathway (Spurgeon. S. L., and Porter, J. W. (1983) in Biosynthesis of Isoprenoid Compounds (Porter, J. W., and Spurgeon, S. L., Eds.), Vol. 1, pp. 1–46, John Wiley, N.Y.).

However, evidence has emerged over the last few years that isopentenyl diphosphate, the central intermediate of isoprenoid biosynthesis, originates from pyruvate and D-glyceraldehyde-3-phosphate via a new mevalonate-independent pathway in several eubacteria (Rohmer, M., et al., *Biochem. J.* 295, 517–524 (1993); Broers, S. T. J. (1994) Ph.D. Thesis, Eidgenössische Technische Hochschule, Zürich, Switzerland; Rohmer, M., et al., *J Am. Chem. Soc.* 118, 2564–2566 (1996)), algae (Schwender, J., et al., *Biochem. J.* 316, 73–80 (1996) ), and plant plastids (Schwarz, M. K. (1994) Ph.D. Thesis, Eidgenössische Technische Hochschule, Zürich, Switzerland; Lichtenthaler, H. K., et al., *FEBS Lett.* 400, 271–274 (1997)). The first step in this novel pathway involves a transketolase-type condensation reaction of pyruvate and glyceraldehyde-3-phosphate to yield 1-deoxy-D-xylulose-5-phosphate (FIG. 1). Genes encoding the enzyme which catalyzes this reaction, deoxyxylulose phosphate synthase, have been cloned from *E. coli* (Sprenger, G. A., et al., *Proc. Natl. Acad Sci. USA* 94, 12857–12862 (1997); Lois, L. M. et al., *Proc. Natl. Acad. Sci. USA* 95, 2105–2110 (1998)), peppermint (*Mentha x piperita*) (Lange, B. M. et al., *Proc. Natl. Acad Sci. USA* 95, 2100–2104 (1998)) and pepper (Bouvier, F. et al., *Plant Physiol.* 117, 1423–1431 (1998)).

The second step of the mevalonate-independent pathway is considered to involve an intramolecular rearrangement and subsequent reduction of deoxyxylulose phosphate to yield 2-C-methyl-D-erythritol4-phosphate (Duvold, T. et al., *Tetrahedron Lett.* 38, 4769–4772 (1997); Duvold, T. et al., *Tetrahedron Lett.* 38, 6181–6184 (1997); Sagner, S. et al., *Tetrahedron Lett.* 39, 2091–2094 (1998)) (FIG. 1). Seto and coworkers (Takahashi, S. et al., *Proc. Natl. Acad. Sci. USA* 95, 9879–9884 (1998)) have recently reported the isolation and characterization of a reductoisomerase gene from *E. coli*. The present invention provides a nucleic acid molecule isolated from peppermint that encodes a 1-deoxy-D-xylulose-5-phosphate reductoisomerase.

SUMMARY OF THE INVENTION

In accordance with the foregoing, a cDNA encoding a 1-deoxy-D-xylulose-5-phosphate reductoisomerase from peppermint (*Mentha piperita*) has been isolated and sequenced, and the corresponding amino acid sequence has been deduced. Accordingly, the present invention relates to isolated DNA sequences which code for the expression of plant 1-deoxy-D-xylulose-5-phosphate reductoisomerase, such as isolated DNA sequences which code for the expression of 1-deoxy-D-xylulose-5-phosphate reductoisomerase from essential oil plants, including plants of the genus Mentha. A representative example of an isolated, Mentha DNA sequence which codes for the expression of 1-deoxy-D-xylulose-5-phosphate reductoisomerase is set forth in SEQ ID NO:1 which encodes a 1-deoxy-D-xylulose-5-phosphate reductoisomerase protein (SEQ ID NO:2) from peppermint (*Mentha piperita*). Additionally, the present invention relates to isolated plant 1-deoxy-D-xylulose-5-phosphate reductoisomerase proteins (including isolated 1-deoxy-D-xylulose-5-phosphate reductoisomerase proteins from essential oil plants, such as plants of the genus Mentha), including the peppermint (*Mentha piperita*) 1-deoxy-D-xylulose-5-phosphate reductoisomerase protein having the amino acid sequence set forth in SEQ ID NO:2.

In another aspect, the present invention relates to nucleic acid molecules that hybridize under stringent conditions to the nucleic acid molecule having the sequence set forth in SEQ ID NO:1, or to its complement, ie., to an antisense molecule that is complementary in sequence to the sequence set forth in SEQ ID NO:1. In other aspects, the present invention is directed to replicable recombinant cloning vehicles comprising a nucleic acid sequence, e.g., a DNA sequence which codes for a plant 1-deoxy-D-xylulose-5-phosphate reductoisomerase, or for a nucleotide sequence sufficiently complementary to at least a portion of DNA or RNA encoding a plant 1-deoxy-D-xylulose-5-phosphate reductoisomerase to enable hybridization therewith (e.g., antisense RNA or fragments of DNA complementary to a portion of DNA or RNA molecules encoding a plant 1-deoxy-D-xylulose-5-phosphate reductoisomerase which are useful as polymerase chain reaction primers or as probes for plant 1-deoxy-D-xylulose-5-phosphate reductoisomerase genes or related genes). In yet other aspects of the invention, modified host cells are provided that have been transformed, transfected, infected and/or injected with a recombinant cloning vehicle and/or DNA sequence of the invention.

Thus, the present invention provides for the recombinant expression of plant 1-deoxy-D-xylulose-5-phosphate reductoisomerase, and the inventive concepts may be used to facilitate the production, isolation and purification of significant quantities of recombinant 1-deoxy-D-xylulose-5-phosphate reductoisomerase (or of its primary enzyme products) for subsequent use, to obtain expression or enhanced expression of 1-deoxy-D-xylulose-5-phosphate reductoisomerase in plants, microorganisms or animals, or may be otherwise employed in an environment where the regulation or expression of 1-deoxy-D-xylulose-5-phosphate reductoisomerase is desired for the production of this enzyme, or its enzyme product, or derivatives thereof.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
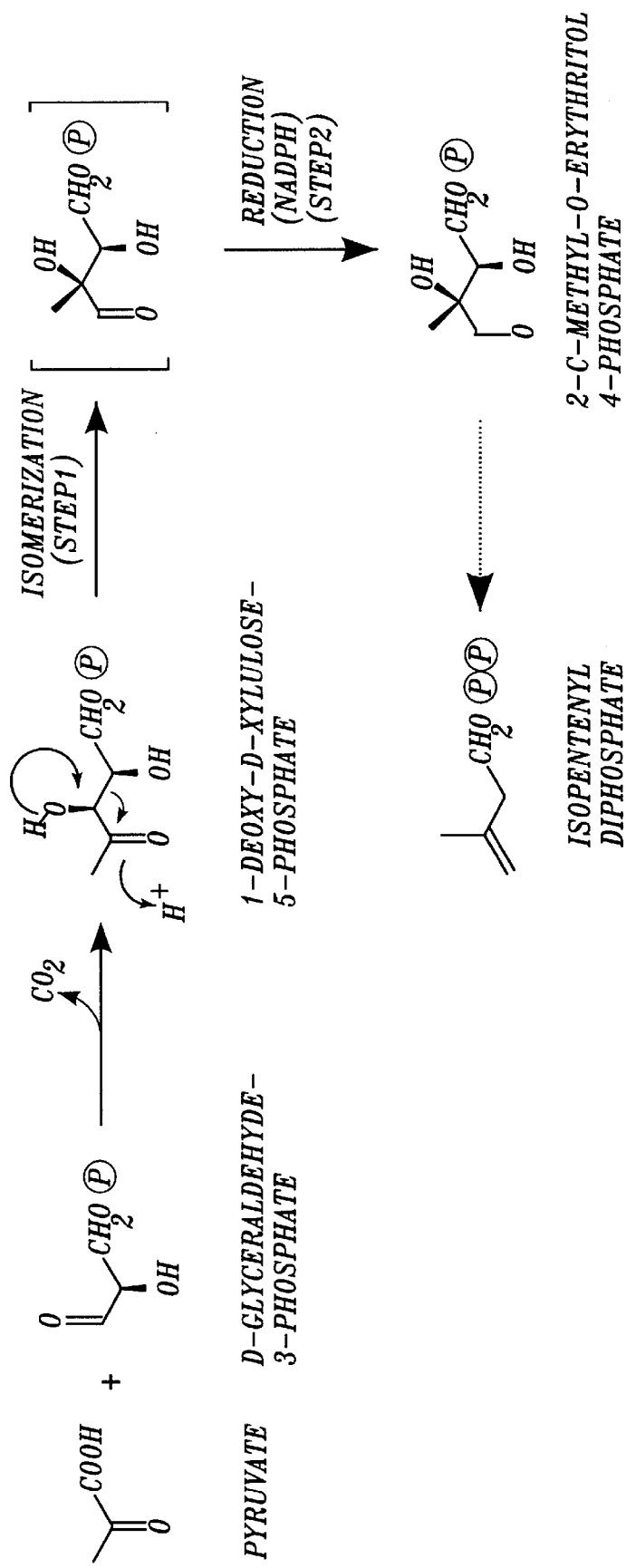
FIG. 1 shows an outline of the pyruvate/glyceraldehyde-3-phosphate pathway for the biosynthesis of isopentenyl diphosphate, and proposed reaction mechanism of the 1-deoxy-D-xylulose-5-phosphate reductoisomerase in the conversion of 1-deoxy-D-xylulose-5-phosphate to 2-C-methyl-D-erythritol-4-phosphate. The circled P denotes the phosphate moiety. The broken arrow indicates several as yet unidentified steps.

As used herein, the terms "amino acid" and "amino acids" refer to all naturally occurring L-α-amino acids or their residues. The amino acids are identified by either the single-letter or three-letter designations:

| Asp | D | aspartic acid |
|-----|---|---------------|
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Ile | I | isoleucine |
| Leu | L | leucine |
| Tyr | Y | tyrosine |
| Phe | F | phenylalanine |
| His | H | histidine |
| Lys | K | lysine |
| Arg | R | arginine |
| Trp | W | tryptophan |
| Gln | Q | glutamine |
| Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "1-deoxy-D-xylulose-5-phosphate reductoisomerase" is used herein to mean an enzyme capable of forming 2-C-methyl-D-erythritol-4-phosphate from 1-deoxy-D-xylulose-5-phosphate.

The term "hybridize under stringent conditions", and grammatical equivalents thereof, means that a nucleic acid molecule that has hybridized to a target nucleic acid molecule immobilized on a DNA or RNA blot (such as a Southern blot or Northern blot) remains hybridized to the immobilized target molecule on the blot during washing of the blot under stringent conditions. In this context, exemplary hybridization conditions are: hybridization in 5×SSC at 65° C. for 16 hours. Exemplary high stringency wash conditions are two washes in 2×SSC at 23° C. for 20 minutes per wash, followed by one wash in 2.0×SSC at 50° C. for 30 minutes. Exemplary very high stringency wash conditions are two washes in 2×SSC at 23° C. for 15 minutes per wash, followed by two washes in 1.0×SSC at 60° C. for 20 minutes.

The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

The term "essential oil plant," or "essential oil plants," refers to a group of plant species that produce high levels of monoterpenoid and/or sesquiterpenoid and/or diterpenoid oils, and/or high levels of monoterpenoid and/or sesquiterpenoid and/or diterpenoid resins. The foregoing oils and/or resins account for greater than about 0.005% of the fresh weight of an essential oil plant that produces them. The essential oils and/or resins are more fully described, for example, in E. Guenther, The Essential Oils, Vols. I–VI, R. E. Krieger Publishing Co., Huntington N.Y., 1975, incorporated herein by reference. The essential oil plants include, but are not limited to:

Lamiaceae, including, but not limited to, the following species: Ocimum (basil), Lavandula (Lavender), Origanum (oregano), Mentha (mint), Salvia (sage), Rosmarinus, (rosemary), Thymus (thyme), Satureja (savory), Monarda (balm) and Melissa.

Umbelliferae, including, but not limited to, the following species: Carum (caraway), Anethum (dill), foeniculum (fennel) and Daucus (carrot).

Asteraceae (Compositae), including, but not limited to, the following species: Artemisia (tarragon, sage brush), Tanacetum (tansy).

Rutaceae (e.g., Citrus plants); Rosaceae (e.g., roses); Myrtaceae (e.g., Eucalyptus, Melaleuca); the Gramineae (e.g., Cymbopogon (citronella)); Geranaceae (Geranium) and certain conifers including Abies (e.g., Canadian balsam), Cedrus (cedar), Thuja, Juniperus, Pinus (pines) and Picea (spruces).

The range of essential oil plants is more fully set forth in E. Guenther, *The Essential Oils, Vols.* I–VI, R. E. Krieger Publishing Co., Huntington N.Y., 1975, which is incorporated herein by reference.

The terms "alteration", "amino acid sequence alteration", "variant" and "amino acid sequence variant" refer to 1-deoxy-D-xylulose-5-phosphate reductoisomerase molecules with some differences in their amino acid sequences as compared to the corresponding, native, i.e., naturally-occurring, 1-deoxy-D-xylulose-5-phosphate reductoisomerases. Ordinarily, the variants will possess at least about 70% homology with the corresponding native 1-deoxy-D-xylulose-5-phosphate reductoisomerases, and preferably, they will be at least about 80% homologous with the corresponding, native 1-deoxy-D-xylulose-5-phosphate reductoisomerases. The amino acid sequence variants of the 1-deoxy-D-xylulose-5-phosphate reductoisomerases falling within this invention possess substitutions, deletions, and/or insertions at certain positions. Sequence variants of 1-deoxy-D-xylulose-5-phosphate reductoisomerases may be used to attain desired enhanced or reduced enzymatic activity, modified regiochemistry or stereochemistry, or altered substrate utilization or product distribution.

Substitutional 1-deoxy-D-xylulose-5-phosphate reductoisomerase variants are those that have at least one amino acid residue in the native 1-deoxy-D-xylulose-5-phosphate reductoisomerase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the 1-deoxy-D-xylulose-5-phosphate reductoisomerase molecules of the present invention may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the 1-deoxy-D-xylulose-5-phosphate reductoisomerase molecules of the present invention would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional 1-deoxy-D-xylulose-5-phosphate reductoisomerase variants are those with one or more amino acids inserted immediately adjacent to an amino acid at a particular position in the native 1-deoxy-D-xylulose-5-phosphate reductoisomerase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native 1-deoxy-D-xylulose-5-phosphate reductoisomerase molecules have been removed. Ordinarily, deletional variants will have one or two amino acids deleted in a particular region of the 1-deoxy-D-xylulose-5-phosphate reductoisomerase molecule. Deletional variants include those where all or most of the transit sequence has been removed.

The terms "biological activity", "biologically active", "activity" and "active" refer to the ability of the 1-deoxy-D-xylulose-5-phosphate reductoisomerases of the present invention to catalyze the formation of 2-C-methyl-D-erythritol-4-phosphate by reduction and rearrangement of 1-deoxy-D-xylulose-5-phosphate. 1-Deoxy-D-xylulose-5-phosphate reductoisomerase activity is measured in an enzyme activity assay, such as the assay described in Example 3 herein. Amino acid sequence variants of the 1-deoxy-D-xylulose-5-phosphate reductoisomerases of the present invention may have desirable altered biological activity including, for example, altered reaction kinetics, substrate utilization, product distribution or other characteristics such as regiochemistry and stereochemistry.

The terms "DNA sequence encoding", "DNA encoding" "nucleic acid molecule encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable vector" "replicable expression vector" and "expression vector" refer to a piece of DNA, usually double-stranded, which may have inserted into it another piece of DNA (the insert DNA) such as, but not limited to, a cDNA molecule. The vector is used to transport the insert DNA into a suitable host cell. The insert DNA may be derived from the host cell, or may be derived from a different cell or organism. Once in the host cell, the vector can replicate independently of or coincidental with the host chromosomal DNA, and several copies of the vector and its inserted DNA may be generated. The terms "replicable expression vector" and "expression vector" refer to replicable vectors that contain the necessary elements that permit transcription and translation of the insert DNA into a polypeptide. Many molecules of the polypeptide encoded by the insert DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of E. coli. Typical eukaryotic host cells are plant cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

Other abbreviations used are: bp, base pair; GC, gas chromatography; HPLC, high performance liquid chromatography; IPTG, isopropyl-1-thio-β-D-galactopyranoside; kb, kilobase pairs; MS., mass spectrometry; Tris, Tris-(hydroxymethyl)aminomethane.

In accordance with the present invention, cDNAs encoding 1-deoxy-D-xylulose-5-phosphate reductoisomerase from Peppermint (*Mentha x piperita*) were isolated and sequenced in the following manner. A cDNA library was constructed from mRNA from isolated peppermint oil gland secretory cells, a cell type highly specialized for essential oil biosynthesis. PCR primers were designed (P1, 5'-CGAGATTATGCCAGGAGAGC-3' (SEQ ID NO:3); P2, 5'-GGCTTCAGGCAAACCCTTG-3' and employed with peppermint oil gland library cDNA as template to amplify a 223 bp fragment designated pMPDXR1 (SEQ ID NO:5) with some similarity (~50%) to the *E. coli* reductoisomerase gene. By screening the peppermint oil gland cDNA library ($2.5 \times 10^4$ plaques) with a labeled probe derived from pMP-DXR1 (SEQ ID NO:5), five full-length clones were obtained, including the cDNA having the nucleic acid sequence set forth in SEQ ID NO:1.

Additionally, cDNA molecules encoding 1-deoxy-D-xylulose-5-phosphate reductoisomerase were isolated from *Arabidopsis thaliana* in the following manner. $2\times10^4$ plaques of an *A. thaliana* flower bud cDNA library (CD4–6 from the Arabidopsis Biological Resource Center (http://aims.cps.msu.edu/aims/)) were screened with pMPDXR1 (SEQ ID NO:5) and afforded 20 positive clones, including the clone having the sequence set forth in SEQ ID NO:6 encoding the 5'-truncated protein having the amino acid sequence set forth in SEQ ID NO:7.

The full-length peppermint 1-deoxy-D-xylulose-5-phosphate reductoisomerase cDNA (having the sequence set forth in SEQ ID NO:1) expressed a functional 1-deoxy-D-xylulose-5-phosphate reductoisomerase protein (SEQ ID NO:2) in *E. coli*, as described in Example 3 herein.

The isolation of cDNAs encoding 1-deoxy-D-xylulose-5-phosphate reductoisomerase from peppermint permits development of efficient expression systems for this functional enzyme; provides useful tools for examining the developmental regulation of 1-deoxy-D-xylulose-5-phosphate reductoisomerase; permits investigation of the reaction mechanism(s) of this enzyme, and permits the isolation of other 1-deoxy-D-xylulose-5-phosphate reductoisomerases, such as other plant 1-deoxy-D-xylulose-5-phosphate reductoisomerases. The isolation of 1-deoxy-D-xylulose-5-phosphate reductoisomerase cDNAs also permits the transformation of a wide range of organisms in order to enhance, or otherwise alter, isoprenoid synthesis and metabolism.

For example, in one aspect the present invention provides methods of enhancing the level of expression of 1-deoxy-D-xylulose-5-phosphate reductoisomerase in a host cell (such as a plant cell) including the step of introducing into a host cell a replicable expression vector that includes a nucleic acid molecule that encodes a 1-deoxy-D-xylulose-5-phosphate reductoisomerase protein under conditions that enable expression of the 1-deoxy-D-xylulose-5-phosphate reductoisomerase in the host cell. By way of representative example, in addition to the nucleic acid molecule having the sequence set forth in SEQ ID NO:1 herein, nucleic acid molecules encoding the 1-deoxy-D-xylulose-5-phosphate reductoisomerase protein reported in Schwender et al., FEBS Letters 455(1–2):140–144 (1999), which publication is incorporated herein by reference, are useful in this aspect of the invention. The Schwender et al protein is deposited in the Genbank database under the Genbank Accession No. CAB43344. In one embodiment of this aspect of the invention, nucleic acid sequences that encode 1-deoxy-D-xylulose-5-phosphate reductoisomerase hybridize under stringent conditions to the antisense complement of the nucleic acid sequence set forth in SEQ ID NO:1.

Again by way of non-limiting example, in another aspect the present invention provides methods of reducing the level of expression of 1-deoxy-D-xylulose-5-phosphate reductoisomerase in a host cell (such as a plant cell) including the step of introducing into a host cell a replicable expression vector that includes a nucleic acid molecule that hybridizes under stringent conditions to the nucleic acid sequence set forth in SEQ ID NO:1. Thus, for example, in addition to the antisense complement of the nucleic acid sequence set forth in SEQ ID NO:1 herein, representative nucleic acid molecules useful in this aspect of the invention include the antisense complements of the following nucleic acid molecules (identified by their Genbank database accession numbers): AI781096, AW256284, AW065057, AW286486, AI727207, AI901056.

Although the 1-deoxy-D-xylulose-5-phosphate reductoisomerase protein encoded by the peppermint cDNA, disclosed herein, direct the enzyme to plastids, substitution of the presumptive targeting sequence of this enzyme with other transport sequences well known in the art (See, for example, the following publications, the cited portions of which are incorporated by reference herein: von Heijne et al., *Eur. J. Biochem.*, 180:535–545, 1989; Stryer, *Biochemistry*, W. H. Freeman and Company, New York, N.Y., p. 769 [1988]) may be employed to direct 1-deoxy-D-xylulose-5-phosphate reductoisomerase to other cellular or extracellular locations.

In addition to native, plant 1-deoxy-D-xylulose-5-phosphate reductoisomerase amino acid sequences, sequence variants produced by deletions, substitutions, mutations and/or insertions and truncations are intended to be within the scope of the invention except insofar as limited by the prior art. The 1-deoxy-D-xylulose-5-phosphate reductoisomerase amino acid sequence variants of this invention may be constructed by mutating the DNA sequences that encode the wild-type enzymes, such as by using techniques commonly referred to as site-directed mutagenesis. Nucleic acid molecules encoding the 1-deoxy-D-xylulose-5-phosphate reductoisomerases of the present invention can be mutated by a variety of PCR techniques well known to one of ordinary skill in the art. (See, for example, the following publications, the cited portions of which are incorporated by reference herein: "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, N.Y. (1990).

By way of non-limiting example, the two primer system utilized in the Transformer Site-Directed Mutagenesis kit from Clontech, may be employed for introducing site-directed mutants into the 1-deoxy-D-xylulose-5-phosphate reductoisomerase genes of the present invention. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather. than prepare each positional mutant separately, a set of "designed degenerate" oligo-nucleotide primers can be synthesized in order to introduce all of the desired mutations at a given site simultaneously. Transformants can be screened by sequencing the plasmid DNA through the mutagenized region to identify and sort mutant clones. Each mutant DNA can then be fully sequenced or restricted and analyzed by electrophoresis on Mutation Detection Enhancement gel (J. T. Baker) to confirm that no other alterations in the sequence have occurred (by band shift comparison to the unmutagenized control).

Again, by way of non-limiting example, the two primer system utilized in the QuikChange™ Site-Directed Mutagenesis kit from Stratagene (LaJolla, Calif.), may be employed for introducing site-directed mutants into the 1-deoxy-D-xylulose-5-phosphate reductoisomerase genes of the present invention. Double-stranded plasmid DNA, containing the insert bearing the target mutation site, is denatured and mixed with two oligonucleotides complementary to each of the strands of the plasmid DNA at the target mutation site. The annealed oligonucleotide primers are extended using Pfu DNA polymerase, thereby generating a mutated plasmid containing staggered nicks. After temperature cycling, the unmutated, parental DNA template is digested with restriction enzyme DpnI which cleaves methylated or hemimethylated DNA, but which does not cleave unmethylated DNA. The parental, template DNA is almost always methylated or hemimethylated since most strains of E. coli, from which the template DNA is obtained, contain the required methylase activity. The remaining, annealed vector DNA incorporating the desired mutation(s) is transformed into E. coli.

The mutated 1-deoxy-D-xylulose-5-phosphate reductoisomerase gene can be cloned into a pET (or other) overexpression vector that can be employed to transform E. coli such as strain E. coli BL21(DE3)pLysS, for high level production of the mutant protein, and purification by standard protocols. Examples of plasmid vectors and E. coli strains that can be used to express high levels of the 1-deoxy-D-xylulose-5-phosphate reductoisomerase proteins of the present invention are set forth in Sambrook et al, *Molecular Cloning, A Laboratory Manual*, 2nd Edition (1989), Chapter 17, incorporated herein by reference. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore BPLC (reversed phase or ion exchange, again depending on the specific region to be modified) to provide several peptides in each fraction, and the molecular weights of the peptides are determined by FAB–MS. The masses are then compared to the molecular weights of peptides expected from the digestion of the predicted sequence, and the correctness of the sequence quickly ascertained. Since the exemplary mutagenesis techniques set forth herein produce site-directed mutations, sequencing of the altered peptide should not be necessary if the mass spectrograph agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

In the design of a particular site directed mutagenesis experiment, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that is usefully altered, although aromatics can also be substituted for alkyl side chains. Changes in the normal product distribution can indicate which step(s) of the reaction sequence have been altered by the mutation. Modification of the hydrophobic pocket can be employed to change binding conformations for substrates and result in altered regiochemistry and/or stereochemistry.

Other site directed mutagenesis techniques may also be employed with the nucleotide sequences of the invention. For example, restriction endonuclease digestion of DNA followed by ligation may be used to generate deletion variants of 1-deoxy-D-xylulose-5-phosphate reductoisomerase, as described in section 15.3 of Sambrook et al. *Molecular Cloning: A Laboratory Manual*, 2nd Ed., Cold Spring Harbor Laboratory Press, New York, N.Y. [1989], incorporated herein by reference. A similar strategy may be used to construct insertion variants, as described in section 15.3 of Sambrook et al., supra.

Oligonucleotide-directed mutagenesis may also be employed for preparing substitution variants of this invention, as well as truncations. It may also be used to conveniently prepare the deletion and insertion variants of this invention. This technique is well known in the art as described by Adelman et al. (*DNA* 2:183 [1983]); Sambrook et al., supra; "Current Protocols in Molecular Biology", 1991, Wiley (N.Y.), F. T. Ausubel, R. Brent, R. E. Kingston, D. D. Moore, J. D. Seidman, J. A. Smith and K. Struhl, eds, incorporated herein by reference.

Generally, oligonucleotides of at least 25 nucleotides in length are used to insert, delete or substitute two or more nucleotides in the 1-deoxy-D-xylulose-5-phosphate reductoisomerase molecule. An optimal oligonucleotide will have 12 to 15 perfectly matched nucleotides on either side of the nucleotides coding for the mutation To mutagenize wild-type 1-deoxy-D-xylulose-5-phosphate reductoisomerase, the oligonucleotide is annealed to the single-stranded DNA template molecule under suitable hybridization conditions. A DNA polymerizing enzyme, usually the Klenow fragment of E. coli DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type enzyme inserted in the vector, and the second strand of DNA encodes the mutated form of the enzyme inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired. amino acid substitutions. If, however, the. amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type 1-deoxy-D-xylulose-5-phosphate reductoisomerase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

A gene (or other nucleic acid molecule) encoding 1-deoxy-D-xylulose-5-phosphate reductoisomerase may be incorporated into any organism (intact plant, animal, microbe, etc.), or cell culture derived therefrom. The enzyme 1-deoxy-D-xylulose-5-phosphate reductoisomerase catalyzes the first committed step in the conversion of 1-deoxy-D-xylulose-5-phosphate to isopentenyl diphosphate which, in turn, is converted to a variety of molecules including, for example, carotenoids, and the prenyl side chains of chlorophyll, plastoquinone and tocopherols. Thus, a 1-deoxy-D-xylulose-5-phosphate reductoisomerase gene (or other nucleic acid molecule) may be introduced into any organism for a variety of purposes including, but not limited to: production of 1-deoxy-D-xylulose-5-phosphate reductoisomerase, or its product 2-C-methyl-D-erythritol-4-phosphate; enhancement of chlorophyll production by increasing the synthesis of the phytol side-chain; enhancement of production of terpenoids, phytoalexins, toxins, and deterrent compounds to improve defense against pathogens, insects and other herbivores; enhance the production of monoterpene flavor and aroma compounds in essential oil plants, fruits and vegetables to improve the flavor and aroma profiles, or improve the yield of flavor and aroma compounds extracted from plants; to prepare synthetic intermediates in plants and microbes for industrial uses, such as the synthesis of adhesives, inks and polymers; to enhance the production of natural pigments, such as carotenoids, in plants, and to improve the yield of natural pigments extracted from plants for medicinal or culinary uses; to enhance the yield in plants of compounds having anti-cancer or other nutraceutical properties, such as vitamin A and vitamin E; and to produce 2C-methyl-D-erythritol phosphate as an enzymatic or chemical intermediate. While the nucleic acid molecules of the present invention can be introduced into any organism, the nucleic acid molecules of the present invention will preferably be introduced into a plant species.

Eukaryotic expression systems may be utilized for the production of 1-deoxy-D-xylulose-5-phosphate reductoisomerase since they are capable of carrying out any required posttranslational modifications and of directing the enzyme to the proper cellular compartment. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures*. [1986]; Luckow et al., *Bio-technology*, 6:47–55 [1987]) for expression of the 1-deoxy-D-xylulose-5-phosphate reductoisomerases of the invention. Infection of insect cells (such as cells of the species *Spodoptera frugiperda*) with the recombinant baculoviruses allows for the production of large amounts of the 1-deoxy-D-xylulose-5-phosphate reductoisomerase proteins. In addition, the baculovirus system has other important advantages for the production of recombinant 1-deoxy-D-xylulose-5-phosphate reductoisomerase. For example, baculoviruses do not infect humans and can therefore be safely handled in large quantities. In the baculovirus system, a DNA construct is prepared including a DNA segment encoding 1-deoxy-D-xylulose-5-phosphate reductoisomerase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/1-deoxy-D-xylulose-5-phosphate reductoisomerase combination is flanked on both sides by 200–300 base pairs of baculovirus DNA (the flanking sequences).

To produce the 1-deoxy-D-xylulose-5-phosphate reductoisomerase DNA construct, a cDNA clone encoding the full length 1-deoxy-D-xylulose-5-phosphate reductoisomerase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full 1-deoxy-D-xylulose-5-phosphate reductoisomerase. For example, an insect host cell can be cotransfected or transfected separately with the DNA construct and a flunctional baculovirus. Resulting recombinant baculoviruses can then be isolated and used to infect cells to effect production of the 1-deoxy-D-xylulose-5-phosphate reductoisomerase. Host insect cells include, for example, *Spodoptera frugiperda* cells, that are capable of producing a baculovirus-expressed 1-deoxy-D-xylulose-5-phosphate reductoisomerase. Insect host cells infected with a recombinant baculovirus of the present invention are then cultured under conditions allowing expression of the baculovirus-encoded 1-deoxy-D-xylulose-5-phosphate reductoisomerase. 1-deoxy-D-xylulose-5-phosphate reductoisomerase thus produced is then extracted from the cells using methods known in the art.

Other eukaryotic microbes such as yeasts may at so be used to practice this invention. The baker's yeast *Saccharomyces cerevisiae*, is a commonly used yeast, although several other strains are available. The plasmid YRp7 (Stinchcomb et al.; *Nature*, 282:39 [1979]; Kingsman et al., *Gene* 7:141 [1979]; Tschemper et al., *Gene*, 10:157 [1980]) is commonly used as an expression vector in Saccharomyces. This plasmid contains the trp 1 gene that provides a selection marker for a mutant strain of yeast lacking the ability to grow in tryptophan, such as strains ATCC No. 44,076 and PEP4-1 (Jones, *Genetics*, 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA*, 75:1929 [1978]). Additional yeast transformation protocols are set forth in Gietz et al., *N.A.R.*, 20(17):1425(1992); Reeves et al., *FEMS*, 99(2–3):193–197, (1992), both of which publications are incorporated herein by reference.

Suitable promoting sequences in yeast vectors include the promoters for 3-phosphoglycerate kinase (Hitzeman et al.,*J.*

*Biol. Chem.*, 255:2073 [1980]) or other glycolytic enzymes (Hess et al., *J. Adv. Enzyme* Reg. 7:149 [1968]; Holland et al., *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes -responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode 1-deoxy-D-xylulose-5-phosphate reductoisomerase and a selectable marker gene, e.g., the kan gene encoding resistance to kanamycin, into *Agrobacterium tumifaciens* containing a helper Ti plasmid as described in Hoeckema et al., *Nature*, 303:179–181 [1983] and culturing the Agrobacterium cells with leaf slices, or other tissues or cells, of the plant to be transformed as described by An et al., *Plant Physiology*, 81:301–305 [1986]. Transformation of cultured plant host cells is normally accomplished through *Agrobacterium tumifaciens*. Cultures of mammalian host cells and other host cells that do not have rigid cell membrane barriers are usually transformed using the calcium phosphate method as originally described by Graham and Van der Eb (*Virology*, 52:546 [1978]) and modified as described in sections 16.32–16.37 of Sambrook et al., supra. However, other methods for introducing DNA into cells such as Polybrene (Kawai and Nishizawa, *Mol. Cell. Biol.*, 4:1172 [1984]), protoplast fusion (Schaffner, *Proc. Natl. Acad. Sci. USA*, 77:2163 [1980]), electroporation (Neumann et al., *EMBO J.*, 1:841 [1982]), and direct microinjection into nuclei (Capecchi, *Cell*, 22:479 [1980]) may also be used. Additionally, animal transformation strategies are reviewed in Monastersky G. M. and Robl, J. M., *Strategies in Transgenic Animal Science*, ASM Press, Washington, D.C., 1995, incorporated herein by reference. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating 1-deoxy-D-xylulose-5-phosphate reductoisomerase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology*, 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a 1-deoxy-D-xylulose-5-phosphate reductoisomerase gene that previously has had its native promoter removed. This engineered gene is the combination of a promoter that responds to an external chemical stimulus and a gene responsible for successful production of 1-deoxy-D-xylulose-5-phosphate reductoisomerase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. [1993], incorporated by reference herein). Representative examples include electroporation-facilitated DNA uptake by protoplasts in which an electrical pulse transiently permeabilizes cell membranes, permitting the uptake of a variety of biological molecules, including recombinant DNA (Rhodes et al., *Science*, 240(4849) :204–207 [1988]); treatment of protoplasts with polyethylene glycol (Lyznik et al., *Plant Molecular Biology*, 13:151–161 [1989]); and bombardment of cells with DNA-laden microprojectiles which are propelled by explosive force or compressed gas to penetrate the cell wall (Klein et al., *Plant Physiol.* 91:440–444 [1989] and Boynton et al., *Science*, 240(4858):1534–1538 [1988]). Transformation of woody species can be achieved, for example, by employing the methods set forth in Han et al, *Plant Science*, 95:187–196 (1994), incorporated herein by reference. A method that has been applied to Rye plants (*Secale cereale*) is to directly inject plasmid DNA, including a selectable marker gene, into developing floral tillers (de la Pena et al., *Nature* 325:274–276 (1987)). Further, plant viruses can be used as vectors to transfer genes to plant cells. Examples of plant viruses that can be used as vectors to transform plants include the Cauliflower Mosaic Virus (Brisson et al., *Nature* 310: 511–514 (1984); Additionally, plant transformation strategies and techniques are reviewed in Birch, R. G., *Ann Rev Plant Phys Plant Mol Biol*, 48:297 (1997); Forester et al., *Exp. Agric.*, 33:15–33 (1997). Numerous publications describe transformation techniques that have been successfully applied to mint (Mentha) species. Representative publications disclosing mint transformation techniques are: A. Spencer et al., *Phytochemistry* 32: 911–919 (1993); C. Berry et al., *Plant Cell Tissue Organ Cult.* 44: 177–181 (1996); J. C. Caissard et al., *Plant Cell Rep.* 16: 67–70 (1996); X. Niu et al., *Plant Cell Rep.* 17: 165–171 (1998); F. Diemer et al., *Plant Sci.* 138: 101–108 (1998). The aforementioned publications disclosing plant transformation techniques are incorporated herein by reference, and minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes.

A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the 0-glucuronidase gene (GUS). The presence of this gene is characterized using a histochemical reaction in which a sample of putatively transformed cells is treated with a GUS assay solution. After an appropriate incubation, the cells containing the GUS gene turn blue.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.*, 36:59 [1977]); baby hamster kidney cells (BHK, ATCC CCL 10); Chinese hamster ovary cells (Urlab and Chasin, *Proc. Natl. Acad Sci USA* 77:4216 [1980]); mouse sertoli cells (TM4, Mather, *Biol. Reprod.*, 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI. 54, Baumann et al., *J. Cell Biol.*, 85:1 [1980]); and TRI cells (Mather et al., *Annals N.Y. Acad. Sci.*, 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature*, 273:113 [1978]). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of 1-deoxy-D-xylulose-5-phosphate reductoisomerase in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-KI cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention, or for expressing the proteins of the present invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No.27,325) *E. coli* X1776 (ATCC No.31,537), and *E. coli* B; however many other strains of *E. coli*, such as HB1O1, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enzymol.*, 204:63 (1991).

As a representative example, cDNA sequences encoding 1-deoxy-D-xylulose-5-phosphate reductoisomerase may be transferred to the (His)$_6$·Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the 1-deoxy-D-xylulose-5-phosphate reductoisomerase again purified by immobilized metal ion affinity chromatography, this time using a shallower imidazole gradient to elute the recombinant reductoisomerase while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature*, 375:615 [1978]; Itakura et al., *Science*, 198:1056 [1977]; Goeddel et al., *Nature*, 281:544 [1979]) and a tryptophan (trp) promoter system (Goeddel et al., *Nucl. Acids Res.*, 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell*, 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W. H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.*, 11:1657 [1983]), α-factor, alkaline phosphatase and invertase may be used to direct secretion from yeast host cells. Prokaryotic signal sequences from genes encoding, for example, LamB or OmpF (Wong et al., *Gene*, 68:193 [1988]), MalE, PhoA, or beta-lactamase, as well as other genes, may be used to target proteins from prokaryotic cells into the culture medium.

Trafficking sequences from plants, animals and microbes can be employed in the practice of the invention to direct the 1-deoxy-D-xylulose-5-phosphate reductoisomerase proteins of the present invention to the cytoplasm, endoplasmic reticulum, mitochondria or other cellular components, or to target the protein for export to the medium. These considerations apply to the overexpression of 1-deoxy-D-xylulose-5-phosphate reductoisomerase, and to direction of expression within cells or intact organisms to permit gene product function in any desired location.

The construction of suitable vectors containing DNA encoding replication sequences, regulatory sequences, phenotypic selection genes and the 1-deoxy-D-xylulose-5-phosphate reductoisomerase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

The 1-deoxy-D-xylulose-5-phosphate reductoisomerase proteins of the present invention can be isolated, for example, by incorporating a nucleic acid molecule of the invention (such as a cDNA molecule) into an expression vector, introducing the expression vector into a host cell and expressing the nucleic acid molecule to yield protein. Representative examples of host cells and expression vectors are as set forth herein. The protein can then be purified by art-recognized means. When a crude protein extract is initially prepared, it may be desirable to include one or more proteinase inhibitors in the extract. Representative examples of proteinase inhibitors include: serine proteinase inhibitors (such as phenylmethylsulfonyl fluoride (PMSF), benzamide, benzamidine HCI, ε-Amino-n-caproic acid and aprotinin (Trasylol)); cysteine proteinase inhibitors, such as sodium p-hydroxymercuribenzoate; competitive proteinase inhibitors, such as antipain and leupeptin; covalent proteinase inhibitors, such as iodoacetate and N-ethylmaleimide; aspartate (acidic) proteinase inhibitors, such as pepstatin and diazoacetylnorleucine methyl ester (DAN); metalloproteinase inhibitors, such as EGTA [ethylene glycol bis(β-aminoethyl ether) N,N,N',N'-tetraacetic acid], and the chelator 1, 10-phenanthroline.

Representative examples of art-recognized techniques for purifying, or partially purifying, proteins from biological material are exclusion chromatography, ion-exchange chromatography, hydrophobic interaction chromatography, reversed-phase chromatography and immobilized metal affinity chromatography.

Hydrophobic interaction chromatography and reversed-phase chromatography are two separation methods based on the interactions between the hydrophobic moieties of a sample and an insoluble, immobilized hydrophobic group present on the chromatography matrix. In hydrophobic interaction chromatography the matrix is hydrophilic and is substituted with short-chain phenyl or octyl nonpolar groups. The mobile phase is usually an aqueous salt solution. In reversed phase chromatography the matrix is silica that has been substituted with longer n-alkyl chains, usually $C_8$ (octylsilyl) or $C_{18}$ (octadecylsilyl). The matrix is less polar than the mobile phase. The mobile phase is usually a mixture of water and a less polar organic modifier.

Separations on hydrophobic interaction chromatography matrices are usually done in aqueous salt solutions, which generally are nondenaturing conditions. Samples are loaded onto the matrix in a high-salt buffer and elution is by a descending salt gradient. Separations on reversed-phase media are usually done in mixtures of aqueous and organic solvents, which are often denaturing conditions. In the case of protein and/or peptide purification, hydrophobic interaction chromatography depends on surface hydrophobic groups and is carried out under conditions which maintain the integrity of the protein molecule. Reversed-phase chromatography depends on the native hydrophobicity of the protein and is carried out under conditions which expose nearly all hydrophobic groups to the matrix, ie., denaturing conditions.

Ion-exchange chromatography is designed specifically for the separation of ionic or ionizable compounds. The stationary phase (column matrix material) carries ionizable functional groups, fixed by chemical bonding to the stationary phase. These fixed charges carry a counterion of opposite sign. This counterion is not fixed and can be displaced. Ion-exchange chromatography is named on the basis of the sign of the displaceable charges. Thus, in anion ion-exchange chromatography the fixed charges are positive and in cation ion-exchange chromatography the fixed charges are negative.

Retention of a molecule on an ion-exchange chromatography column involves an electrostatic interaction between the fixed charges and those of the molecule, binding involves replacement of the nonfixed ions by the molecule. Elution, in turn, involves displacement of the molecule from the fixed charges by a new counterion with a greater affinity for the fixed charges than the molecule, and which then becomes the new, nonfixed ion.

The ability of counterions (salts) to displace molecules bound to fixed charges is a function of the difference in affinities between the fixed charges and the nonfixed charges of both the molecule and the salt. Affinities in turn are affected by several variables, including the magnitude of the net charge of the molecule and the concentration and type of salt used for displacement.

Solid-phase packings used in ion-exchange chromatography include cellulose, dextrans, agarose, and polystyrene. The exchange groups used include DEAE (diethylaminoethyl), a weak base, that will have a net positive charge when ionized and will-therefore bind and exchange anions; and CM (carboxymethyl), a weak acid, with a negative charge when ionized that will bind and exchange cations. Another form of weak anion exchanger contains the PEI (polyethyleneimine) functional group. This material, most usually found on thin layer sheets, is useful for binding proteins at pH values above their pI. The polystyrene matrix can be obtained with quaternary ammonium functional groups for strong base anion exchange or with sulfonic acid functional groups for strong acid cation exchange. Intermediate and weak ion-exchange materials are also available. Ion-exchange chromatography need not be performed using a column, and can be performed as batch ion-exchange chromatography with the slurry of the stationary phase in a vessel such as a beaker.

Gel filtration is performed using porous beads as the chromatographic support. A column constructed from such beads will have two measurable liquid volumes, the external volume, consisting of the liquid between the beads, and the internal volume, consisting of the liquid within the pores of the beads. Large molecules will equilibrate only with the external volume while small molecules will equilibrate with both the external and internal volumes. A mixture of molecules (such as proteins) is applied in a discrete volume or zone at the top of a gel filtration column and allowed to percolate through the column. The large molecules are excluded from the internal volume and therefore emerge first from the column while the smaller molecules, which can access the internal volume, emerge later. The volume of a conventional matrix used for protein purification is typically 30 to 100 times the volume of the sample to be fractionated. The absorbance of the column effluent can be continuously monitored at a desired wavelength using a flow monitor.

A technique that is often applied to the purification of proteins is High Performance Liquid Chromatography (HPLC). HPLC is an advancement in both the operational theory and fabrication of traditional chromatographic systems. BPLC systems for the separation of biological macromolecules vary from the traditional column chromatographic systems in three ways; (1) the column packing materials are of much greater mechanical strength, (2) the particle size of the column packing materials has been decreased 5- to 10-fold to enhance adsorption-desorption kinetics and diminish bandspreading, and (3) the columns are operated at 10–60 times higher mobile-phase velocity. Thus, by way of non-limiting example, HPLC can utilize exclusion chromatography, ion-exchange chromatography, hydrophobic interaction chromatography, reversed-phase chromatography and immobilized metal affinity chromatography. Art-recognized techniques for the purification of proteins and peptides are set forth in Methods in Enzymology, Vol. 182, Guide to Protein Purification, Murray P. Deutscher, ed (1990), which publication is incorporated herein by reference.

In another aspect, the present invention is directed to methods of reducing the level of expression of 1-deoxy-D-xylulose-5-phosphate reductoisomerase protein in a host cell, such as a plant cell. A number of methods can be used to inhibit gene expression in plants. For instance, antisense RNA technology can be conveniently used. The successful implementation of anti-sense RNA in developmental systems to inhibit gene expression has previously been demonstrated (Van der Krol et al., 1990 *Plant Mol. Biol.* 14:457; Visser et al., 1991, *Mol. Gen. Genet.* 225:289; Hamilton et al., 1990, *Nature* 346:284; Stockhaus et al., 1990, *EMBO J.* 9:3013; Hudson et al., 1992, *Plant Physiol.* 98:294; U.S. Pat. Nos.: 4,801,340, 5,773,692, 5,723,761, and 5,959,180). For example, polygalacturonase has been implicated in the process of fruit softening during the latter stages of ripening in tomato (Hiatt et al., 1989 in *Genetic Engineering*, Setlow, ed. p. 49; Sheehy et al., 1988, *Proc. Natl. Acad Sci. USA* 85:8805; Smith et al., 1988, *Nature* 334:724). The integration of anti-sense constructs into the tomato genome, under the control of the CaMV 35S promoter, has resulted in a 90% suppression of gene expression.

The anti-sense gene is a DNA sequence that is inverted relative to its normal orientation for transcription and so expresses an RNA transcript that is complementary to a target mRNA molecule expressed within the host cell (i.e., the RNA transcript of the anti-sense gene. can hybridize to the target mRNA molecule through Watson-Crick base pairing). An anti-sense gene may be constructed in a number of different ways provided that it is capable of interfering with the expression of a target gene, such as a 1-deoxy-D-xylulose-5-phosphate reductoisomerase gene. The anti-sense gene can be constructed by inverting the coding region (or a portion thereof) of the target gene relative to its normal orientation for transcription to allow the transcription of its complement, hence the RNAs encoded by the anti-sense and sense gene are complementary.

The anti-sense gene generally will be substantially identical to at least a portion of the target gene or genes. The sequence, however, need not be perfectly identical to inhibit expression. Generally, higher homology can be used to compensate for the use of a shorter anti-sense gene. The anti-sense gene generally will be substantially identical (although in antisense orientation) to the target gene. The minimal identity will typically be greater than about 65%, but a higher identity might exert a more effective repression of expression of the endogenous sequences. Substantially greater identity of more than about 80% is preferred, though about 95% to absolute identity would be most preferred.

Furthermore, the anti-sense gene need not have the same intron or exon pattern as the target gene, and non-coding segments of the target gene may be equally effective in achieving anti-sense suppression of target gene expression as coding segments. Normally, a DNA sequence of at least about 30 or 40 nucleotides should be used as the anti-sense gene, although a longer sequence is preferable. The construct is then transformed into one or more plant cells (from which whole plants can be regenerated as described herein) and the antisense strand of RNA is produced.

Catalytic RNA molecules or ribozymes can also be used to inhibit expression of target genes. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. (1988 *Nature*, 334:585–591)(see also U.S. Pat. No. :5,646,023), both of which publications are incorporated herein by reference. Tabler et al. (1991, *Gene* 108:175) have greatly simplified the construction of catalytic RNAs by combining the advantages of the antisense RNA and the ribozyme technologies in a single construct. Smaller regions of homology are required for ribozyme catalysis, therefore this can promote the repression of different members of a large gene family if the cleavage sites are conserved.

Another method of suppressing target gene expression is sense suppression. Introduction of a nucleic acid molecule configured in the sense orientation has been recently shown to be an effective means by which to block the transcription of target genes. For an example of the use of this method to modulate expression of endogenous genes see, Napoli et al., (1990 *Plant Cell* 2:279–289), and U.S. Pat. Nos. 5,034,323, 5,231,020, 5,283,184 and 5,942,657, each of which publications are incorporated herein by reference. For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence may compensate for a longer, less identical sequence. Furthermore, the introduced sequence need not have the same intron or exon pattern, and identity of non-coding segments will be equally effective. Normally, a sequence of the size ranges noted above for antisense regulation is used.

More recently, a new method of suppressing the expression of a target gene has been developed. This method involves the introduction into a host cell of an inverted repeat transgene that directs the production of mRNAs that self-anneal to form double stranded (ds) RNA structures (Vionnet et al., 1998 *Cell* 95:177–187; Waterhouse et al., 1998 *Proc. Natl. Acad. Sci. USA* 95:13959–13964; Misquitta et al., 1999 *Proc. Natl. Acad Sci. USA* 96:1451–1456; Baulcombe, 1999 *Current Opinion Plant Biol.* 2:109–113; Sharp, 1999 Genes and Develop. 13:139–141). The ds RNA molecules, in a manner not understood, interfere with the post transcriptional expression of endogenous genes that are homologous to the dsRNA. It has been shown that the region of dsRNA homology must contain a region that is homologous to an exon portion of the target gene. Thus, the dsRNA may include sequences that are homologous to noncoding portions of the target gene. Alternatively, gene suppressive dsRNA could also be produce by transforming a cell with two different transgenes, one expressing a sense RNA and the other a complementary antisense RNA.

A construct containing an inverted repeat of a transcribed sequence of a target gene can be made, for example, by following the guidance provided by Waterhouse et al.(1998), supra. The inverted repeat part of the construct comprises about 200 to 1500 bp of transcribed DNA repeated in a head to head or tail to tail arrangement. The repeats are separated by about 200 to 1500 bp of non repeated DNA which can also be part of the transcribed region of the target gene, or can be from a different gene, and perhaps contain an intron. A suitable inverted repeat construct may be made by attaching in the following order: a plant promoter; a 3' region from a target cDNA oriented in the "sense" orientation; a 5' region from the target cDNA; the same 3' region of the target cDNA coding sequence but oriented in "anti-sense" orientation; and finally a polyA addition signal. The transcribed RNA resulting from introduction of the inverted repeat transgene into a target plant will have the potential of forming an internal dsRNA region containing sequences from the target gene that is to be suppressed. The dsRNA sequences are chosen to suppress a single, or perhaps multiple, target gene(s). In some cases, the sequences with the potential for dsRNA formation may originate from two or more related, target genes (e.g., members of a gene family).

An additional strategy suitable for suppression of target gene activity entails the sense expression of a mutated or partially deleted form of the protein encoded by the target gene according to general criteria for the production of dominant negative mutations (Herskowitz I, *Nature* 329: 219–222 (1987)). Examples of strategies that produced dominant negative mutations are provided (Mizukami, 1996; Emmler, 1995; Sheen, 1998; and Paz-Ares, 1990).

Wild-type target gene function can also be eliminated or diminished by using DNA regions flanking the target gene to mediate an insertional disruption of the target gene coding sequence (Miao et al., 1995; *Plant J.* 7:359–365; Kempin et al., 1997 *Nature* 389:802–803). The targeted gene replacement is mediated by homologous recombination between sequences in a transformation vector that includes DNA regions flanking the target gene and the corresponding chromosomal sequences. A selectable marker, such as kanamycin, bar or pat, or a screenable marker, such as beta-glucuronidase (GUS), is included in between the target gene flanking regions. These markers facilitate the identification of cells that have undergone target gene replacement.

The following examples merely illustrate the best mode now contemplated for practicing the invention, but should not be construed to limit the invention.

EXAMPLE 1

Isolation of a cDNA Molecule Encoding a 1-deoxy-D-xylulose-5-phosphate Reductoisomerase from Peppermint (*Mentha piperita*)

A cDNA library was constructed from mRNA from isolated peppermint oil gland secretory cells, a cell type highly specialized for essential oil biosynthesis (Lange, B. M., and Croteau, R. (1999) *Curr. Opin. Plant Biol.* 2:139–144 (1999)). Based on likely conserved regions of the reductoisomerase gene, PCR primers were designed (P1, 5'-CGAGATTATGCCAGGAGAGC-3' (SEQ ID NO:3); P2, 5'-GGCTTCAGGCAAACCCTTG-3' (SEQ ID NO:4)) and employed with peppermint oil gland library cDNA as template to amplify a 223 bp fragment designated pMDDXR1 (SEQ ID NO:5) with significant homology to the *E. coli* reductoisomerase gene. By screening the peppermint oil gland cDNA library ($2.5 \times 10^4$ plaques) with a labeled probe derived from pMPDXR1 (SEQ ID NO:5), five full-length clones were obtained, including the cDNA molecule having the nucleic acid sequence set forth in SEQ ID NO:1.

EXAMPLE 2

Isolation of a cDNA Molecule Encoding a 1-deoxy-D-xylulose-5-phosphate Reductoisomerase from *Arabidopsis thaliana*

$2 \times 10^4$ plaques of an *A. thaliana* flower bud cDNA library (CD4–6 from the Arabidopsis Biological Resource Center (http://aims.cps.msu.edu/aims/)) were screened with pMPDXR1 (SEQ ID NO:5) and afforded 20 positive clones, such as the cDNA molecule having the sequence set forth in SEQ ID NO:6, all of which were slightly 5'-truncated. The conditions for screening the *A. thaliana* flower bud cDNA library were: hybridization in 5×SSC at 65° C. for 16 hours, followed by two washes in 2×SSC at room temperature for 20 minutes per wash, then one wash in 1×SSC at 55° C. for 30 minutes.

EXAMPLE 3

Functional expression of 1-deoxy-D-xylulose-5-phosphate reductoisomerases from Peppermint (*Mentha piperita*) and *E. coli*

An additional primer set (P3, 5'-GTCTCAACTCTGGAAGCTTTATGAAGCAACTCT AC-3'; (SEQ ID NO:8) and P4, 5'-CTCTGTAGCCGGACCTAGGTCAGCTTGCGAGAC-3' (SEQ ID NO:9)) was employed to amplify a full-length *E. coli* reductoisomerase gene, and the resulting amplicon was inserted into pBluescript KS(–) for use as a positive control in the functional expression of the enzyme.

The full-length peppermint 1-deoxy-D-xylulose-5-phosphate reductoisomerase cDNA (designated pMPDXR18 (SEQ ID NO:1)) and the *E. coli* reductoisomerase clone (pECDXR20) were evaluated by expression in *E. coli* for the ability to catalyze the rearrangement and pyridine nucleotide-dependent reduction of 1-deoxy-D-xylulose-5-phosphate to 2-C-methyl-D-erythritol4-phosphate.

Figure 2A:
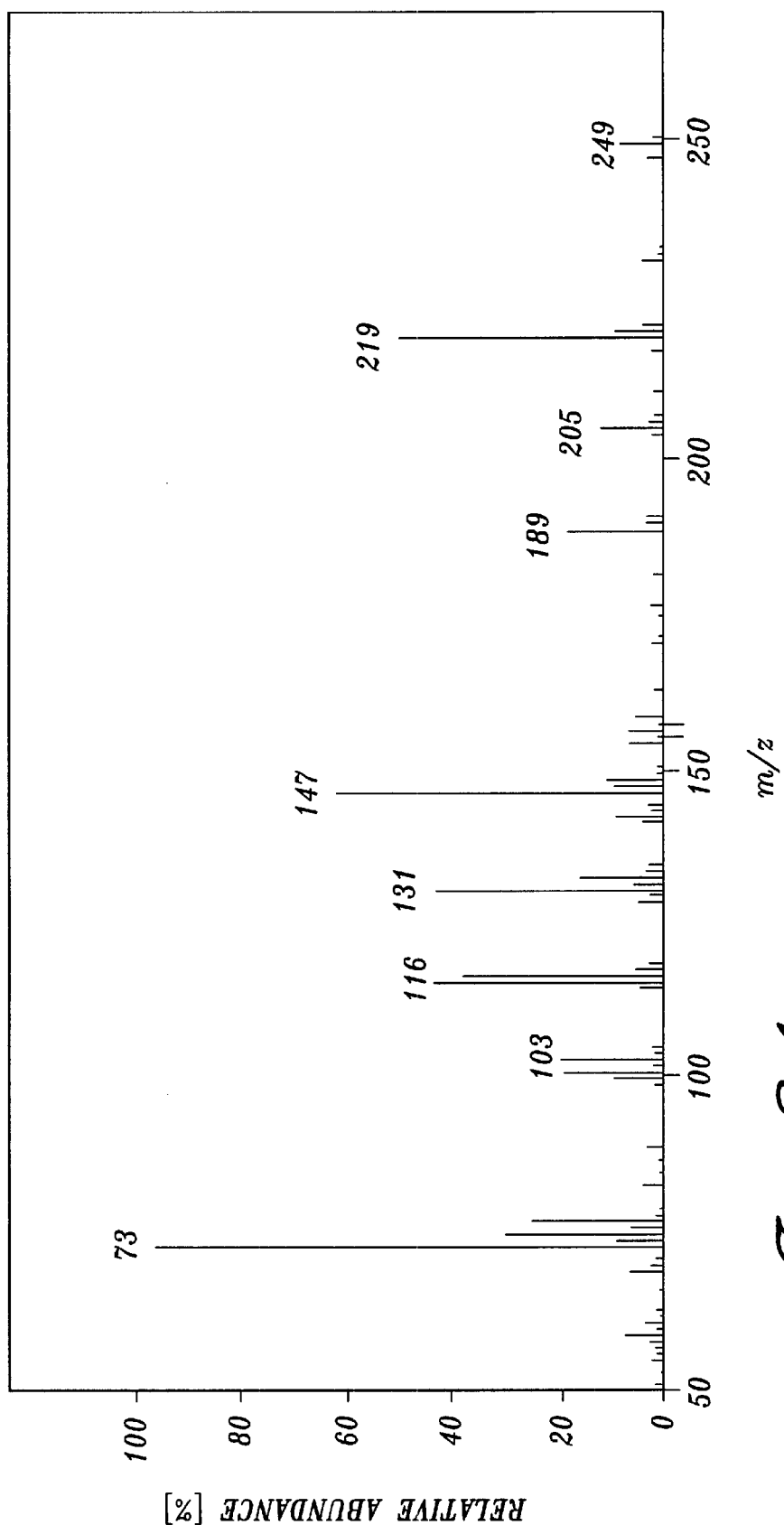
FIG. 2 shows GC-MS analysis of (A) the trimethylsilyl ether derivative of the dephosphorylated biosynthetic product ($R_t$=7.1±0.1 min) generated by recombinant peppermint 1-deoxy-D-xylulose-5-phosphate reductoisomerase (SEQ ID NO:2), and (B) the trimethylsilyl ether derivative of authentic 2-C-methyl-D,L-erythritol ($R_t$=7.1±0.1 min) identically prepared.
Figure 2B:
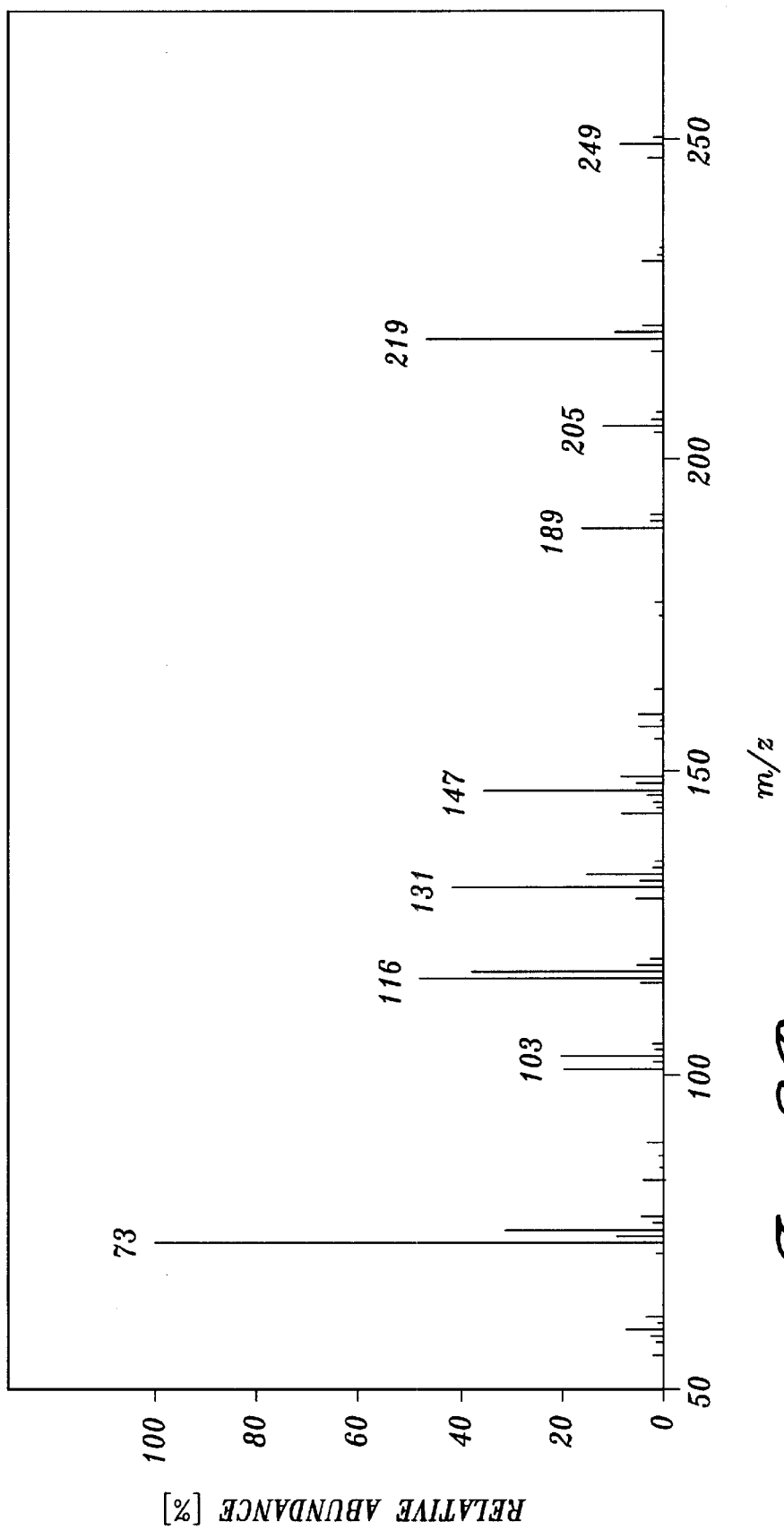

FIG. 2 shows GC-MS analysis of (A) the trimethylsilyl ether derivative of the dephosphorylated biosynthetic product ($R_t$=7.1±0.1 min) generated by recombinant peppermint 1-deoxy-D-xylulose-5-phosphate reductoisomerase (SEQ ID NO:2), and (B) the trimethylsilyl ether derivative of authentic 2-C-methyl-D,L-erythritol ($R_t$=7.1±0.1 min) identically prepared. The slight difference in relative intensity of ions in the mn/z 116, 131, 147 cluster in spectrum A is due to background subtraction of contaminants in the case of the biosynthetic product for which the total ion abundance was tenfold less than for the standard (B). For enzyme preparation, transformed *E. coli* cells were grown to $A_{600}$ of 0.5 at 37° C. in 50 ml of Luria-Bertani medium supplemented with appropriate antibiotics. Cells harboring the peppermint 1-deoxy-D-xylulose-5-phosphate reductoisomerase cDNA (SEQ ID NO:1) were then incubated at 20° C. for 2 h, induced with 0.1 mM IPTG, and maintained at 20° C. for 15 h. Cells harboring a nucleic acid sequence encoding 1-deoxy-D-xylulose-5-phosphate reductoisomerase from *E. coli* were similarly induced, but with 1 mM IPTG, and maintained at 37° C. for 5 h. Bacteria were harvested by centrifugation, washed with 1 ml of assay buffer (0.1 M Tris/HCl (pH 7.5) containing 2 mM $MnCl_2$ and 0.5 mM NADPH), resuspended in 1 ml of assay buffer, and then disrupted by brief sonication at 0–4° C. The resulting homogenates were centrifuged to pellet debris, and an aliquot (15 μl) of each preparation was incubated with 0.1 mmol [1-$^{14}$C]deoxyxylulose phosphate (18.5 kBq) for 10 min at 23° C. To the reaction mixtures, 50 μl of 10 mM $NaHCO_3$ was added, the suspensions were filtered through Nanosep columns (Pall Filtron; 30,000 kDa cut-off), and the filtrates were analyzed by modification of an established reversed-phase ion-pair radio-BPLC method (McCaskill, D. and Croteau, R., *Anal. Biochem.* 215: 142–149 (1998)) using 10 mM tetrabutylammonium acetate as ion-pairing reagent. Enzyme assays from both sources revealed the presence of a new radiolabeled product at $R_t$=34.0 min, which was isolated by semipreparative HPLC as above. Following solvent removal under vacuum, the residual material was dissolved in 50 μl of 0.1 M potassium phosphate buffer (pH 5.0) to which 10 units of wheat germ acid phosphatase were added (Sigma) followed by incubation at 23° C. for 2 h. The reaction was terminated by addition of 50 μl of acetone, followed by centrifugation, transfer of the supernatant and removal of solvent under vacuum. The residual material was dissolved in 20 μl of anhydrous diethyl ether and converted to the trimethylsilyl ether derivative for GC-MS analysis as previously described (Lange, B. M. et al., *Proc. Natl. Acad. Sci. USA* 95, 2100–2104 (1998)). The mass spectra of the products derived from the recombinant peppermint 1-deoxy-D-xylulose-5-phosphate reductoisomerase (SEQ ID NO:2) and *E. coli* reductoisomerase were identical.

The derivatized product from both sources exhibited the same retention time (7.1±0.1 min) and mass spectrum as an authentic sample of 2-C-methyl-D,L-erythritol identically derivatized (FIG. 2B), thereby confirming the identity of the plant 1-deoxy-D-xylulose-5-phosphate reductoisomerase (SEQ ID NO:2) and indicating that the plant enzyme (SEQ ID NO:2) is active in the preprotein form.

The reaction catalyzed by ketol acid reductoisomerase, which the reaction catalyzed by 1-deoxy-D-xylulose-5-phosphate reductoisomerase resembles, obeys an ordered mechanism in which NADPH and the metal ion cofactor bind first, followed by the acetohydroxy acid substrate (Chunduru, S. K. et al., *Biochemistry* 28, 486–493 (1989)). Since NADPH and manganese (or magnesium) are also required for the enzymatic conversion of deoxyxylulose phosphate to methylerythritol phosphate (no intermediates, such as methylerythrose phosphate, were observed in the presence or absence of these cofactors), a similar reaction mechanism may be postulated for deoxyxylulose phosphate reductoisomerase.

EXAMPLE 4

Sequence Analysis of 1-deoxy-D-xylulose-5-phosphate reductoisomerase from Peppermint (*Mentha piperita*)

The peppermint 1-deoxy-D-xylulose-5-phosphate reductoisomerase cDNA (SEQ ID NO:1) contains an open reading frame of 1425 bp encoding a protein of 475 deduced amino acid residues (SEQ ID NO:2). The first 73 amino acids display typical characteristics of plastidial targeting sequences (von Heijne, G.et al., *Eur. J. Biochem.* 180, 535–545 (1989)), consistent with the subcellular localization of this enzyme in plant plastids where the mevalonate-independent pathway operates (Schwarz, M. K. (1994) Ph.D. Thesis, Eidgenössische Technische Hochschule, Zürich, Switzerland; Lichtenthaler, H. K., Schwender, J., Disch, A. and Rohmer, M. (1997) *FEBS Lett.* 400, 271–274.). When the residues defining the putative transit peptide are excluded, the size of the mature enzyme is estimated at about 43.5 kDa. Alignment of translated sequences (devoid of plastidial targeting peptides where appropriate) reveals significant homology between the peppermint 1-deoxy-D-xylulose-5-phosphate reductoisomerase (SEQ ID NO:2) and the putative 1-deoxy-D-xylulose-5-phosphate reductoisomerase fragment from *A. thaliana* (SEQ ID NO:7) (88.0% similarity/84.2% identity), as well as with SLL0019 from the cyanobacterium *Synechocystis* sp. PCC6803 (72.3/63.7%), BG13409 from *Bacillus subtilis* (56.9/45.5%), the reductoisomerase of *E. coli* (53.4/43.0%), HI0807 from *Haemophilus influenzae* (55.5/41.8%), Rv2870c from *Mycobacterium tuberculosis* (52.8/43.6%), and HP0216 from *Helicobacter pylori* (50.7/38.1%). The peppermint cDNA (SEQ ID NO:2) also shows significant homology to a highly truncated, Arabidopsis cDNA fragment of unknown function (SEQ ID NO:10), deposited in the Genbank database as Accession Number T43949, and to the exon portions of an Arabidopsis genomic clone of unknown function (SEQ ID NO:11), deposited in the Genbank database as Accession Number AB009053. Note that SEQ ID NO:11 sets forth the sequence of the negative (i.e., non-coding) strand of the Arabidopsis genomic clone.

Although the reaction mechanism of 1-deoxy-D-xylulose-5-phosphate reductoisomerase and of ketol acid reductoisomerase, which catalyzes the rearrangement and reduction of 2-acetolactate to 2,3-dihydroxyisovalerate and of 2-aceto-2-hydroxybutyrate to 2,3-dihydroxy-3-methylvalerate in the biosynthesis of branched-chain amino acids (Mrachko, G. T. et al., *Arch. Biochem. Biophys.* 294, 446–453 (1992)), share some similarity, the deduced amino acid sequences of these enzymes are quite distinct (~35% similarity). However, the N-terminus of the 1-deoxy-D-xylulose-5-phosphate reductoisomerase sequences contains a conserved motif (GSTGSIG)(SEQ ID NO:12) with some homology to the signature sequence of the proposed NADPH binding site of ketol acid reductoisomerase (GXGXXGXXXG)(SEQ ID NO:13) (Rane, M. J., and Calvo, K. C., *Arch. Biochem. Biophys.* 338, 83–89 (1997)).

The isolation of cDNAs encoding both deoxyxylulose phosphate synthase (Lange, B. M. et al., *Proc. Natl. Acad. Sci. USA* 95, 2100–2104 (1998)) and 1-deoxy-D-xylulose-5-phosphate reductoisomerase (SEQ ID NO:1) from peppermint provides substantial evidence for the operation of similar catalytic machinery in the pyruvate/glyceraldehyde-3-phosphate pathway in plant plastids and several eubacteria. Since this essential pathway is present in plants and bacteria but apparently not in animals, both the synthase and reductoisomerase are targets for the development of novel classes of highly specific herbicides, antimalarials (Jomaa, D. et al., *Science* 285:1573–1576 (1999) and antibiotics (Kuzuyama, T. et al., *Tetrahedron Lett.* 39, 7913–7916 (1998)). Whereas deoxyxylulose phosphate serves as the precursor for the biosynthesis of thiamin (Julliard, J. H., and Douce, R. *Proc. Natl. Acad Sci. USA* 88, 2042–2045 (1991)) and probably pyridoxol (Hill, R. E. et al., *J. Biol. Chem.* 271, 30426–30435 (1996)) in higher plants, as well as isopentenyl diphosphate (McCaskill, D., and Croteau, R., *Tetrahedron Letts.* 40, 653–656 (1999)), the 1-deoxy-D-xylulose-5-phosphate reductoisomerase catalyzes the first committed step in the conversion of this common intermediate to plastidial isoprenoids, including carotenoids and the prenyl side-chains of chlorophyll and plastoquinone (Bouvier, F. et al., *Plant Physiol.* 117,1423–1431 (1998)). This specific transformation may be expected to be a regulated (and potentially rate-limiting) step of isoprenoid biosynthesis in plastids.

EXAMPLE 5

Physical Properties of Presently Preferred 1-deoxy-D-xylulose-5-phosphate Reductoisomerase Proteins of the Present Invention Table 1 sets forth physical properties of presently preferred 1-deoxy-D-xylulose-5-phosphate reductoisomerase proteins of the present invention.

TABLE 1

| | |
|---|---|
| Native Molecular Weight of Monomeric protein (excluding transit peptide) | 40,000 to 45,000 |
| pI | 5.5 to 6.0 |
| pH optimum | 7.0 to 8.0 |
| Cofactor Utilization | Requires divalent metal cation (e.g., $Mn^{2+}$, $Mg^{2+}$) and a reduced pyridine nucleotide (NADPH or possibly NADH) |

EXAMPLE 6

Hybridization of a Portion of the Peppermint (*Mentha x piperita*) 1-deoxy-D-xylulose-5-phosphate Reductoisomerase cDNA (SEQ ID NO:1) to Other Nucleic Acid Sequences of the Present Invention The portion of the peppermint 1-deoxy-D-xylulose-5-phosphate reductoisomerase cDNA clone (SEQ ID NO:1) extending from nucleotide 230 to nucleotide 1496, and its complementary nucleic acid strand, were radiolabelled and used to probe a filter bearing RNA samples isolated from the following plants: *Arabidopsis thaliana* leaf tissue; tomato (*Lycopersicon esculentum*) leaf tissue; corn (*Zea mays*) leaf tissue; and Grand fir (*Abies grandis*) needles. Hybridization and washing were conducted by utilizing the technique of hybridizing radiolabelled nucleic acid probes to nucleic acids immobilized on nitrocellulose filters or nylon membranes as set forth at pages 9.52 to 9.55 of Molecular Cloning, A Laboratory Manual (2nd edition), J. Sambrook, E. F. Fritsch and T. Maniatis eds, the cited pages of which are incorporated herein by reference. Hybridization was in 3×SSC at 65° C. for 16 hours, followed by two washes in 2×SSC at 23° C. for 20 minutes per wash, followed by one wash in 0.5×SSC at 55C for 30 minutes.

A single mRNA band was detected in each RNA sample in the predicted 1.7 to 2.0 kb size range. The predicted size of the mRNAs corresponding to the cloned peppermint (SEQ ID NO:1) and Arabidopsis (SEQ ID NO:6) cDNAs is approximately 1.7kb. These results demonstrate that the sequences of mRNA molecules encoding 1-deoxy-D-xylulose-5-phosphate reductoisomerase are highly conserved amongst a broad range of phylogenetically distant plant species.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated plant 1-deoxy-D-xylulose-5-phosphate reductoisomerase protein.

2. An isolated essential oil plant 1-deoxy-D-xylulose-5-phosphate reductoisomerase protein of claim 1.

3. An isolated Mentha 1-deoxy-D-xylulose-5-phosphate reductoisomerase protein of claim 1.

4. An isolated Mentha 1-deoxy-D-xylulose-5-phosphate reductoisomerase protein of claim 3, said protein comprising the amino acid sequence set forth in SEQ ID NO:2.

* * * * *

UNITED STATES PATENT AND TRADEMARK OFFICE
CERTIFICATE OF CORRECTION

PATENT NO. : 6,420,159 B2
DATED : July 16, 2002
INVENTOR(S) : R.B. Croteau et al.

It is certified that error appears in the above-identified patent and that said Letters Patent is hereby corrected as shown below:

Column 1,
Line 19, "DE-FG00-96ER20212," should read -- DE-FG03-96ER20212, --

Signed and Sealed this

Twenty-ninth Day of June, 2004

JON W. DUDAS
*Acting Director of the United States Patent and Trademark Office*

SEQUENCE LISTING

```
<160> NUMBER OF SEQ ID NOS: 13

<210> SEQ ID NO 1
<211> LENGTH: 1759
<212> TYPE: DNA
<213> ORGANISM: Mentha piperita
<220> FEATURE:
<221> NAME/KEY: CDS
<222> LOCATION: (72)..(1496)

<400> SEQUENCE: 1
agaaagcacc tttctatttt cttcagcttt ctgcacattt gagcttgtga ttaaccatgg      60
ctctaaactt g atg gct cta aac ttg atg gct cca act gaa atc aag act      110
            Met Ala Leu Asn Leu Met Ala Pro Thr Glu Ile Lys Thr
              1               5                  10 ctc tct ttc ttg gat agc tcc aaa tcg aat tac aat ctc aat cct ctc      158
Leu Ser Phe Leu Asp Ser Ser Lys Ser Asn Tyr Asn Leu Asn Pro Leu
       15                  20                  25 aag ttc caa ggt gga ttt gct ttt aag agg aag gat agt aga tgc act      206
Lys Phe Gln Gly Gly Phe Ala Phe Lys Arg Lys Asp Ser Arg Cys Thr
 30                  35                  40                  45 gct gca aag aga gtc cat tgc tca gca cag tca cag tca ccg cct ccg      254
Ala Ala Lys Arg Val His Cys Ser Ala Gln Ser Gln Ser Pro Pro Pro
                 50                  55                  60 gct tgg ccc gga cgg gct ttt ccc gag ccc ggt cgt atg act tgg gag      302
Ala Trp Pro Gly Arg Ala Phe Pro Glu Pro Gly Arg Met Thr Trp Glu
             65                  70                  75 ggc ccg aag ccc att tca gtt att ggc tcc act ggc tcc att gga act      350
Gly Pro Lys Pro Ile Ser Val Ile Gly Ser Thr Gly Ser Ile Gly Thr
         80                  85                  90 cag acg ctc gac ata gtt gct gaa aat ccg gat aaa ttt aga atc gtc      398
Gln Thr Leu Asp Ile Val Ala Glu Asn Pro Asp Lys Phe Arg Ile Val
     95                 100                 105 gca ctt gca gct ggt tca aat gtc acc ctc ctt gct gat cag aag gct      446
Ala Leu Ala Ala Gly Ser Asn Val Thr Leu Leu Ala Asp Gln Lys Ala
110                 115                 120                 125 ttc aaa cct aaa tta gta tca gta aaa gac gag tcg tta att agt gag      494
Phe Lys Pro Lys Leu Val Ser Val Lys Asp Glu Ser Leu Ile Ser Glu
                130                 135                 140 ctc aaa gaa gct ctg gct ggt ttc gaa gat atg cct gaa att att cca      542
Leu Lys Glu Ala Leu Ala Gly Phe Glu Asp Met Pro Glu Ile Ile Pro
            145                 150                 155 gga gag cag ggg atg atc gag gtt gct cgc cat cca gat gct gtt act      590
Gly Glu Gln Gly Met Ile Glu Val Ala Arg His Pro Asp Ala Val Thr
        160                 165                 170
```

```
gta gta acg gga att gtc ggc tgt gca ggt ttg aag ccg aca gtg gct      638
Val Val Thr Gly Ile Val Gly Cys Ala Gly Leu Lys Pro Thr Val Ala
    175                 180                 185 gcc ata gaa gct gga aag gac att gct ttg gcc aat aaa gag aca cta      686
Ala Ile Glu Ala Gly Lys Asp Ile Ala Leu Ala Asn Lys Glu Thr Leu
190                 195                 200                 205 atc gct gga ggg cct ttt gtc ctt cct ctt gca aag aag cac aac gtc      734
Ile Ala Gly Gly Pro Phe Val Leu Pro Leu Ala Lys Lys His Asn Val
                210                 215                 220 aag att ctt cct gca gac tcc gaa cat tct gct ata ttt cag tgt atc      782
Lys Ile Leu Pro Ala Asp Ser Glu His Ser Ala Ile Phe Gln Cys Ile
                    225                 230                 235 caa ggc ttg cca gaa ggt gct ttg agg cgt ata att ttg act gca tcg      830
Gln Gly Leu Pro Glu Gly Ala Leu Arg Arg Ile Ile Leu Thr Ala Ser
            240                 245                 250 gga gga gct ttc agg gat ttg ccc gtt gag aaa ttg aaa gag gtg aaa      878
Gly Gly Ala Phe Arg Asp Leu Pro Val Glu Lys Leu Lys Glu Val Lys
        255                 260                 265 gta gca gat gct tta aag cat tcc aac tgg aat atg ggg aaa aag aat      926
Val Ala Asp Ala Leu Lys His Ser Asn Trp Asn Met Gly Lys Lys Asn
270                 275                 280                 285 aca gtg cga ctt ctg caa ctc ttc ttt aac aag ggc ctc gaa gtc ata      974
Thr Val Arg Leu Leu Gln Leu Phe Phe Asn Lys Gly Leu Glu Val Ile
                290                 295                 300 aaa gct cac tat ttg ttt ggg gca gaa tat gat gat att gag att gtt     1022
Lys Ala His Tyr Leu Phe Gly Ala Glu Tyr Asp Asp Ile Glu Ile Val
                    305                 310                 315 att cat tcc cca tcc atc att cac tcg atg gtc gag aca cag gat tca     1070
Ile His Ser Pro Ser Ile Ile His Ser Met Val Glu Thr Gln Asp Ser
            320                 325                 330 tcg gtg cta gct caa tta gga tgg ccc gat atg cgt ttg cct att ctg     1118
Ser Val Leu Ala Gln Leu Gly Trp Pro Asp Met Arg Leu Pro Ile Leu
        335                 340                 345 tac acc tta tca tgg cca gag aga gtc tac tgc tcc gag att aca tgg     1166
Tyr Thr Leu Ser Trp Pro Glu Arg Val Tyr Cys Ser Glu Ile Thr Trp
350                 355                 360                 365 cct cga ctc gac ctc tgc aag gtc gat tta cca ttc aag aag ccc gat     1214
Pro Arg Leu Asp Leu Cys Lys Val Asp Leu Pro Phe Lys Lys Pro Asp
                370                 375                 380 aac cgt gaa ata ccc gct atg gat cta gcc tat gct gct tgg aag agc     1262
Asn Arg Glu Ile Pro Ala Met Asp Leu Ala Tyr Ala Ala Trp Lys Ser
                    385                 390                 395 cgg agc acc atg acc gga gtt ctg agc gca gct aat gag aaa gca gtc     1310
Arg Ser Thr Met Thr Gly Val Leu Ser Ala Ala Asn Glu Lys Ala Val
            400                 405                 410 gaa atg ttc atc gac gag aaa atc ggc tac ctc gac att ttc aag gtc     1358
Glu Met Phe Ile Asp Glu Lys Ile Gly Tyr Leu Asp Ile Phe Lys Val
        415                 420                 425 gtg gag ctt aca tgc gac aag cat cga tcg gaa atg gcg gtg tcg cct     1406
Val Glu Leu Thr Cys Asp Lys His Arg Ser Glu Met Ala Val Ser Pro
430                 435                 440                 445 tcg ttg gag gag atc gtt cac tac gac cag tgg gca cgc gac tac gct     1454
Ser Leu Glu Glu Ile Val His Tyr Asp Gln Trp Ala Arg Asp Tyr Ala
                450                 455                 460 gca acg gtg ctg aaa tcg gcc ggt ttg agt cct gct ctt gta              1496
Ala Thr Val Leu Lys Ser Ala Gly Leu Ser Pro Ala Leu Val
                    465                 470                 475 tgagcagagg ttgatgcaaa tttgatcaac tggaagcttg ttccttttc tttttttttg    1556
```

```
ttctggtttt ccttcttact tttagggagg aagccattta ctatgaaaag gaaggaatc    1616 atgtgacttt gtgaaacagt cccaccatga aatagatata aaagaatcac aagattttgt   1676
gttttatgat tttcatcaaa aagtgtaaat tttgatgtct cagattattt gtagcttaaa   1736
aggtgaataa acacagcagt tgg                                           1759
```

<210> SEQ ID NO 2
<211> LENGTH: 475
<212> TYPE: PRT
<213> ORGANISM: Mentha piperita

<400> SEQUENCE: 2

```
Met Ala Leu Asn Leu Met Ala Pro Thr Glu Ile Lys Thr Leu Ser Phe
 1               5                  10                  15

Leu Asp Ser Ser Lys Ser Asn Tyr Asn Leu Asn Pro Leu Lys Phe Gln
            20                  25                  30

Gly Gly Phe Ala Phe Lys Arg Lys Asp Ser Arg Cys Thr Ala Ala Lys
        35                  40                  45

Arg Val His Cys Ser Ala Gln Ser Gln Ser Pro Pro Ala Trp Pro
    50                  55                  60

Gly Arg Ala Phe Pro Glu Pro Gly Arg Met Thr Trp Glu Gly Pro Lys
65                  70                  75                  80

Pro Ile Ser Val Ile Gly Ser Thr Gly Ser Ile Gly Thr Gln Thr Leu
                85                  90                  95

Asp Ile Val Ala Glu Asn Pro Asp Lys Phe Arg Ile Val Ala Leu Ala
            100                 105                 110

Ala Gly Ser Asn Val Thr Leu Leu Ala Asp Gln Lys Ala Phe Lys Pro
        115                 120                 125

Lys Leu Val Ser Val Lys Asp Glu Ser Leu Ile Ser Glu Leu Lys Glu
    130                 135                 140

Ala Leu Ala Gly Phe Glu Asp Met Pro Glu Ile Ile Pro Gly Glu Gln
145                 150                 155                 160

Gly Met Ile Glu Val Ala Arg His Pro Asp Ala Val Thr Val Val Thr
                165                 170                 175

Gly Ile Val Gly Cys Ala Gly Leu Lys Pro Thr Val Ala Ala Ile Glu
            180                 185                 190

Ala Gly Lys Asp Ile Ala Leu Ala Asn Lys Glu Thr Leu Ile Ala Gly
        195                 200                 205

Gly Pro Phe Val Leu Pro Leu Ala Lys Lys His Asn Val Lys Ile Leu
    210                 215                 220

Pro Ala Asp Ser Glu His Ser Ala Ile Phe Gln Cys Ile Gln Gly Leu
225                 230                 235                 240

Pro Glu Gly Ala Leu Arg Arg Ile Ile Leu Thr Ala Ser Gly Gly Ala
                245                 250                 255

Phe Arg Asp Leu Pro Val Glu Lys Leu Lys Glu Val Lys Val Ala Asp
            260                 265                 270

Ala Leu Lys His Ser Asn Trp Asn Met Gly Lys Lys Asn Thr Val Arg
        275                 280                 285

Leu Leu Gln Leu Phe Phe Asn Lys Gly Leu Glu Val Ile Lys Ala His
    290                 295                 300

Tyr Leu Phe Gly Ala Glu Tyr Asp Asp Ile Glu Ile Val Ile His Ser
305                 310                 315                 320

Pro Ser Ile Ile His Ser Met Val Glu Thr Gln Asp Ser Ser Val Leu
                325                 330                 335
```

```
Ala Gln Leu Gly Trp Pro Asp Met Arg Leu Pro Ile Leu Tyr Thr Leu
                340                 345                 350

Ser Trp Pro Glu Arg Val Tyr Cys Ser Glu Ile Thr Trp Pro Arg Leu
        355                 360                 365

Asp Leu Cys Lys Val Asp Leu Pro Phe Lys Lys Pro Asp Asn Arg Glu
    370                 375                 380

Ile Pro Ala Met Asp Leu Ala Tyr Ala Ala Trp Lys Ser Arg Ser Thr
385                 390                 395                 400

Met Thr Gly Val Leu Ser Ala Ala Asn Glu Lys Ala Val Glu Met Phe
                405                 410                 415

Ile Asp Glu Lys Ile Gly Tyr Leu Asp Ile Phe Lys Val Val Glu Leu
                420                 425                 430

Thr Cys Asp Lys His Arg Ser Glu Met Ala Val Ser Pro Ser Leu Glu
            435                 440                 445

Glu Ile Val His Tyr Asp Gln Trp Ala Arg Asp Tyr Ala Ala Thr Val
        450                 455                 460

Leu Lys Ser Ala Gly Leu Ser Pro Ala Leu Val
465                 470                 475

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: PCR primer P1

<400> SEQUENCE: 3
cgagattatg ccaggagagc                                              20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(19)
<223> OTHER INFORMATION: PCR primer P2

<400> SEQUENCE: 4
ggcttcaggc aaacccttg                                               19

<210> SEQ ID NO 5
<211> LENGTH: 270
<212> TYPE: DNA
<213> ORGANISM: Mentha piperita

<400> SEQUENCE: 5
tgaaattatt ccaggagagc aggggatgat cgaggttgct cgccatccag atgctgttac    60
tgtagtaacg ggaattgtcg gctgtgcagg tttgaagccg acagtggctg ccatagaagc   120
tggaaaggac attgctttgg ccaataaaga gacactaatc gctggagggc cttttgtcct   180
tcctcttgca aagaagcaca acgtcaagat tcttcctgca gactccgaac attctgctat   240
atttcagtgt atccaaggct tgccagaagg                                    270

<210> SEQ ID NO 6
```

-continued

```
<211> LENGTH: 1197
<212> TYPE: DNA
<213> ORGANISM: Arabidopsis thaliana
<220> FEATURE:
<221> NAME/KEY: CDS
<222> LOCATION: (1)..(1197)

<400> SEQUENCE: 6 gga cca aaa ccc atc tct atc gtt gga tct act ggt tct att ggc act      48
Gly Pro Lys Pro Ile Ser Ile Val Gly Ser Thr Gly Ser Ile Gly Thr
  1               5                  10                  15 cag aca ttg gat att gtg gct gag aat cct gac aaa ttc aga gtt gtg      96
Gln Thr Leu Asp Ile Val Ala Glu Asn Pro Asp Lys Phe Arg Val Val
             20                  25                  30 gct cta gct gct ggt tcg aat gtt act cta ctt gct gat cag gta agg     144
Ala Leu Ala Ala Gly Ser Asn Val Thr Leu Leu Ala Asp Gln Val Arg
         35                  40                  45 aga ttt aag cct gca ttg gtt gct gtt aga aac gag tca ctg att aat     192
Arg Phe Lys Pro Ala Leu Val Ala Val Arg Asn Glu Ser Leu Ile Asn
     50                  55                  60 gag ctt aaa gag gct tta gct gat ttg gac tat aaa ctc gag att att     240
Glu Leu Lys Glu Ala Leu Ala Asp Leu Asp Tyr Lys Leu Glu Ile Ile
 65                  70                  75                  80 cca gga gag caa gga gtg att gag gtt gcc cga cat cct gaa gct gta     288
Pro Gly Glu Gln Gly Val Ile Glu Val Ala Arg His Pro Glu Ala Val
                 85                  90                  95 acc gtt gtt acc gga ata gta ggt tgt gcg gga cta aag cct acg gtt     336
Thr Val Val Thr Gly Ile Val Gly Cys Ala Gly Leu Lys Pro Thr Val
            100                 105                 110 gct gca att gaa gca gga aag gac att gct ctt gca aac aaa gag aca     384
Ala Ala Ile Glu Ala Gly Lys Asp Ile Ala Leu Ala Asn Lys Glu Thr
        115                 120                 125 tta atc gca ggt ggt cct ttc gtg ctt ccg ctt gcc aac aaa cat aat     432
Leu Ile Ala Gly Gly Pro Phe Val Leu Pro Leu Ala Asn Lys His Asn
    130                 135                 140 gta aag att ctt ccg gca gat tca gaa cat tct gcc ata ttt cag tgt     480
Val Lys Ile Leu Pro Ala Asp Ser Glu His Ser Ala Ile Phe Gln Cys
145                 150                 155                 160 att caa ggt ttg cct gaa ggc gct ctg cgc aag ata atc ttg act gca     528
Ile Gln Gly Leu Pro Glu Gly Ala Leu Arg Lys Ile Ile Leu Thr Ala
                165                 170                 175 tct ggt gga gct ttt agg gat tgg cct gtc gaa aag cta aag gaa gtt     576
Ser Gly Gly Ala Phe Arg Asp Trp Pro Val Glu Lys Leu Lys Glu Val
            180                 185                 190 aaa gta gcg gat gcg ttg aag cat cca aac tgg aac atg gga aag aaa     624
Lys Val Ala Asp Ala Leu Lys His Pro Asn Trp Asn Met Gly Lys Lys
        195                 200                 205 atc act gtg gac tct gct acg ctt ttc aac aag ggt ctt gag gtc att     672
Ile Thr Val Asp Ser Ala Thr Leu Phe Asn Lys Gly Leu Glu Val Ile
    210                 215                 220 gaa gcg cat tat ttg ttt gga gct gag tat gac gat ata gag att gtc     720
Glu Ala His Tyr Leu Phe Gly Ala Glu Tyr Asp Asp Ile Glu Ile Val
225                 230                 235                 240 att cat ccg caa agt atc ata cat tcc atg att gaa aca cag gat tca     768
Ile His Pro Gln Ser Ile Ile His Ser Met Ile Glu Thr Gln Asp Ser
                245                 250                 255 tct gtg ctt gct caa ttg ggt tgg cct gat atg cgt tta ccg att ctc     816
Ser Val Leu Ala Gln Leu Gly Trp Pro Asp Met Arg Leu Pro Ile Leu
            260                 265                 270 tac acc atg tca tgg ccc gat aga gtt cct tgt tct gaa gta act tgg     864
Tyr Thr Met Ser Trp Pro Asp Arg Val Pro Cys Ser Glu Val Thr Trp
```

-continued

| | | | | | | | | | | | | | | | | |
|---|---|---|---|---|---|---|---|---|---|---|---|---|---|---|---|---|
| | | 275 | | | | 280 | | | | | 285 | | | | | |
| cca | aga | ctt | gac | ctt | tgc | aag | ctc | ggt | tca | ttg | act | ttc | aag | aaa | cca | 912 |
| Pro | Arg | Leu | Asp | Leu | Cys | Lys | Leu | Gly | Ser | Leu | Thr | Phe | Lys | Lys | Pro | |
| | 290 | | | | 295 | | | | | 300 | | | | | | |
| gac | aat | gtg | aaa | tac | cca | tcc | atg | gat | ctt | gct | tat | gct | gct | gga | cga | 960 |
| Asp | Asn | Val | Lys | Tyr | Pro | Ser | Met | Asp | Leu | Ala | Tyr | Ala | Ala | Gly | Arg | |
| 305 | | | | | 310 | | | | | 315 | | | | | 320 | |
| gct | gga | ggc | aca | atg | act | gga | gtt | ctc | agc | gcc | gcc | aat | gag | aaa | gct | 1008 |
| Ala | Gly | Gly | Thr | Met | Thr | Gly | Val | Leu | Ser | Ala | Ala | Asn | Glu | Lys | Ala | |
| | | | | 325 | | | | | 330 | | | | | 335 | | |
| gtt | gaa | atg | ttc | att | gat | gaa | aag | ata | agc | tat | ttg | gat | atc | ttc | aag | 1056 |
| Val | Glu | Met | Phe | Ile | Asp | Glu | Lys | Ile | Ser | Tyr | Leu | Asp | Ile | Phe | Lys | |
| | | | 340 | | | | | 345 | | | | | 350 | | | |
| gtt | gtg | gaa | tta | aca | tgc | gat | aaa | cat | cga | aac | gag | ttg | gta | aca | tca | 1104 |
| Val | Val | Glu | Leu | Thr | Cys | Asp | Lys | His | Arg | Asn | Glu | Leu | Val | Thr | Ser | |
| | | 355 | | | | | 360 | | | | | 365 | | | | |
| ccg | tct | ctt | gaa | gag | att | gtt | cac | tat | gac | ttg | tgg | gca | cgt | gaa | tat | 1152 |
| Pro | Ser | Leu | Glu | Glu | Ile | Val | His | Tyr | Asp | Leu | Trp | Ala | Arg | Glu | Tyr | |
| | 370 | | | | | 375 | | | | | 380 | | | | | |
| gcc | gcg | aat | gtg | cag | ctt | tct | tct | ggt | gct | agg | cca | gtt | cat | gca | | 1197 |
| Ala | Ala | Asn | Val | Gln | Leu | Ser | Ser | Gly | Ala | Arg | Pro | Val | His | Ala | | |
| 385 | | | | | 390 | | | | | 395 | | | | | | |

<210> SEQ ID NO 7
<211> LENGTH: 399
<212> TYPE: PRT
<213> ORGANISM: Arabidopsis thaliana

<400> SEQUENCE: 7

Gly Pro Lys Pro Ile Ser Ile Val Gly Ser Thr Gly Ser Ile Gly Thr
  1               5                  10                  15

Gln Thr Leu Asp Ile Val Ala Glu Asn Pro Asp Lys Phe Arg Val Val
             20                  25                  30

Ala Leu Ala Ala Gly Ser Asn Val Thr Leu Leu Ala Asp Gln Val Arg
         35                  40                  45

Arg Phe Lys Pro Ala Leu Val Ala Val Arg Asn Glu Ser Leu Ile Asn
     50                  55                  60

Glu Leu Lys Glu Ala Leu Ala Asp Leu Asp Tyr Lys Leu Glu Ile Ile
 65                  70                  75                  80

Pro Gly Glu Gln Gly Val Ile Glu Val Ala Arg His Pro Glu Ala Val
                 85                  90                  95

Thr Val Val Thr Gly Ile Val Gly Cys Ala Gly Leu Lys Pro Thr Val
            100                 105                 110

Ala Ala Ile Glu Ala Gly Lys Asp Ile Ala Leu Ala Asn Lys Glu Thr
        115                 120                 125

Leu Ile Ala Gly Gly Pro Phe Val Leu Pro Leu Ala Asn Lys His Asn
    130                 135                 140

Val Lys Ile Leu Pro Ala Asp Ser Glu His Ser Ala Ile Phe Gln Cys
145                 150                 155                 160

Ile Gln Gly Leu Pro Glu Gly Ala Leu Arg Lys Ile Ile Leu Thr Ala
                165                 170                 175

Ser Gly Gly Ala Phe Arg Asp Trp Pro Val Glu Lys Leu Lys Glu Val
            180                 185                 190

Lys Val Ala Asp Ala Leu Lys His Pro Asn Trp Asn Met Gly Lys Lys
        195                 200                 205

Ile Thr Val Asp Ser Ala Thr Leu Phe Asn Lys Gly Leu Glu Val Ile
    210                 215                 220

```
Glu Ala His Tyr Leu Phe Gly Ala Glu Tyr Asp Asp Ile Glu Ile Val
225                 230                 235                 240

Ile His Pro Gln Ser Ile Ile His Ser Met Ile Glu Thr Gln Asp Ser
            245                 250                 255

Ser Val Leu Ala Gln Leu Gly Trp Pro Asp Met Arg Leu Pro Ile Leu
        260                 265                 270

Tyr Thr Met Ser Trp Pro Asp Arg Val Pro Cys Ser Glu Val Thr Trp
            275                 280                 285

Pro Arg Leu Asp Leu Cys Lys Leu Gly Ser Leu Thr Phe Lys Lys Pro
        290                 295                 300

Asp Asn Val Lys Tyr Pro Ser Met Asp Leu Ala Tyr Ala Ala Gly Arg
305                 310                 315                 320

Ala Gly Gly Thr Met Thr Gly Val Leu Ser Ala Ala Asn Glu Lys Ala
                325                 330                 335

Val Glu Met Phe Ile Asp Glu Lys Ile Ser Tyr Leu Asp Ile Phe Lys
            340                 345                 350

Val Val Glu Leu Thr Cys Asp Lys His Arg Asn Glu Leu Val Thr Ser
        355                 360                 365

Pro Ser Leu Glu Glu Ile Val His Tyr Asp Leu Trp Ala Arg Glu Tyr
    370                 375                 380

Ala Ala Asn Val Gln Leu Ser Ser Gly Ala Arg Pro Val His Ala
385                 390                 395
```

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(36)
<223> OTHER INFORMATION: PCR primer P3

<400> SEQUENCE: 8
gtctcaactc tggaagcttt atgaagcaac tctcac                            36

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(33)
<223> OTHER INFORMATION: PCR primer P4

<400> SEQUENCE: 9
ctctgtagcc ggacctaggt cagcttgcga gac                               33

<210> SEQ ID NO 10
<211> LENGTH: 295
<212> TYPE: DNA
<213> ORGANISM: Arabidopsis thaliana
<220> FEATURE:
<221> NAME/KEY: misc_feature
<222> LOCATION: (1)..(295)
<223> OTHER INFORMATION: Arabidopsis EST sequence wherein n represents
      an unknown nucleic acid base

<400> SEQUENCE: 10

-continued

```
gctgatttgg actataaact cgagattatn ccaggagagc aaggagtgat tnaggttgcc      60
cgacatcctg aagctgtaac cgttgtnacc ggaatagtag gttgtncggg actaaagcct     120
acggttgctg caattaaagc aggaaaggac attgctcttg caaacaaaga gacattaatc     180
gcaggtggtc ctttcgtgcn tccgcttgcn aacaaacata atgtaaaaga ttctnccggc     240
agattcagaa cattntgnca tatttnaaat gtattcaagg gtttgcctna agccg          295
```

<210> SEQ ID NO 11
<211> LENGTH: 8050
<212> TYPE: DNA
<213> ORGANISM: Arabidopsis thaliana

<400> SEQUENCE: 11

```
atatatatca aaccaatata ttttattatc aagtttcatt acataatgtc tcatactaaa      60
ccaacaaaaa taaacgtcag tatatttagc atatatttac tttgtcagta taccaaccct     120
cattgcttaa tatataatgg aaatcaatct gaagtataac ctacaagttg tacgtgtcta     180
atagtaaacg aagtaccacc ttagataatc tgatatcaca cataatagta attaataagg     240
ttaaattatg aaaagaatga cttgcaagtt acgatttatg ataacttaaa gaagcttttt     300
atcataaacc gaccaattga tttcctggta catttatatt aaaacatcat tattgcaaaa     360
taatgagtcg acaaatcaaa acttctattg ttccaaatcg cttttgccaa acaaattatt     420
aatctaatgt gaaggtgttt tcctatgcta tgactaataa tttagttaaa attattccta     480
atgattttag cggtggcagt aggttaaaaa gagtgcattt atatcttctt ctttttttgg     540
taaggagagt gcatttatat ctttatccct acgattcgta actaaatcct ttaaaaaaga     600
aaaaaaaaac taattgtttt taattcaagt tttattgccg gtattagaaa cagaaaatat     660
ttatttcttg attgtttcaa ataatggaaa ccaaaaaaaa aggaaagaga aattagtaat     720 caaaagtaa atttgaaaga aaaaaagggg aaatcaccat caattaagta aacccatcgc     780
cagagcaaca aaaaccatta tcgccctcgt agcttcttca gtttctcgag tcatctctaa     840
gatacgacgt ttcaagtctc tcaacgatgg aatgtaataa ggaagaagct aaaagagcaa     900
tgactagtca ttgcagagag aaaactttct gagaacgatt acattggtca ttggtgcaaa     960
gaaattcatt aacaaggctc agaatttgta tccaacgctc gatggtttga aacaaccttt    1020
gatgatgatc aatgttttata tctctgcatc aaacaaagaa gaaggagaat ctgactggta    1080
tggaatcctt ggtgttgatc ctttagctga tgatgaaaca gtgaagaaac attacaagac    1140
cttagctctg ttgcttcacc cggacaagaa caggtttaat ggtgcggaag gtgcgtttaa    1200
gctggtttta gatgcttggt ctctactatc tgataaagct aagagaattg cgttgatcaa    1260
aagagaaaac caaaacaaga aaagagcgaa ccatctgctt cgtgtaataa gcctgcagag    1320
cctgcttctt cttcttcgtc gaaaccggtg gacatgacct tttcgacagt gagcatgacc    1380
ttttcgacag tatgcaataa atgcacaacg agatgttgtc attttcgac gcagaatcat    1440 cttaacaaga cctttccttg tccaaactgt ggtcagaatt cggctatgac caatatatca    1500
tcgacagagg tgatcaatgg gaggacattc atcagagtct ctgtttctcc gcaacaagaa    1560
gaaccatcga gggccaattc tcaagcaact agcagacgta gcacacgtca tgatgatgca    1620
aactctactg agagttttttt caagaaacca atgccgacaa caggagatgc aaactctact    1680
catgaagctc agaggctttt caagaaccca atgacgacaa caggagatgc gaactctact    1740
catgaagctc agaggctttt caagaaccct tagatgaatg taattaatca tataatgtga    1800
aacaattaag ctcggtttta ttggtaaaaa tggtttcaaa ttatcagttt ggcttgttcg    1860
```

-continued

```
gatcacagat aaattagcta cacaatccat aatccttgcc aaaaacgcta ttaagtagta    1920
ccccattctc tacactaatc ttctttcaac atttcctcag aagcttcctt atgttcttcc    1980
aacaaccaat tcttcatgca tgaactggcc tagcaccaga agaaagctgc acattcgcgg    2040
catattcacg tgcccacaag tcatagtgaa caatctcttc aagagacggt gatgttacca    2100
actcgtttcg atgtttatcg catgttaatt ccacaacctt gaagatatcc aaatagctta    2160
tcctgtaaac aaaagtgaga atataaacaa ttgtgattcg tatcaagaac ttcattgaga    2220
tgctcaaaac tgaaaataa ttcttacttt tcatcaatga acatttcaac agctttctca     2280
ttggcggcgc tgagaactcc agtcattgtg cctccagctc gtccagcagc ataagcaaga    2340
tccatggatg ggtatttcac attgtctggt ttcttgaaag tcaatgaacc gagtctgcca    2400
aaatccacaa ttgtaaacaa cttttggttt taggtgctga atgctgatag ataaggcagt    2460
ggtcctaacc cagtttaact gatccacacc aaaacagtag caaaataacc aattgcaaaa    2520
ccaaaccgaa gaccgattcg gtttcatttt ttatcttatc taaacaacct aaaaccaaac    2580
tgaaaacaag attggggaac ttttcttggt gataattaaa attttcaact aagcttagct    2640
tcacacttga taaacagaga gtatataaat gtggttagct tacttgcaaa ggtcaagtct    2700
tggccaagtt acttcagaac aaggaactct atcgggccat gacatggtgt agagaatcgg    2760
taaacgcata tcaggccaac ccaattgagc aagcacagat gaatcctgtg aacaaaaca     2820 aatacatgtt atacagttat ttttttaaaa ccggaaaaat aataatttag ttagtaatgt    2880
ttcagcaaga cctgtgtttc aatcatggaa tgtatgatac tttgcggatg aatgacaatc    2940
tctatatcgt catactcagc tccaaacaaa taatgcgctt caatgacctc aagaccctgt    3000
ttcaaaaaat caagaactca tctaccttga tcaaaggtat tttcaaaatc agagtttaac    3060
cttaggagaa aataatctta accttgttga aaagcgtagc agagtccaca gtgattttct    3120
ttcccatgtt ccagtttgga tgcttcaacg catccgctac tttaacttcc tttagctttt    3180
cgacaggcca atccctttt caaaatccag tgaaaagttt ccattaacca aacgagaatt     3240
gagaagaaaa aaagtctatg cagagagaga agaatatcga aacaaaccta aaagctccac    3300
cagatgcagt caagattatc ttgcgcagag cgccttcagg caaaccttga atacactaga    3360
gaacataaaa gaagattttt cactcaaatt gccagaggtt gaacttgcat taagaccaac    3420
gctgaactca atatgaaagt tgaggtactt aattctatgt gatttgtgat acctgaaata    3480
tggcagaatg ttctgaatct gccggaagaa tctttacatt atgtttgttg gcaagcggaa    3540
gcacgaaagg accacctgcg attaatgtct cttttgtttgc aagagcaatg tcctttcctg    3600
cttcaattgc agcaaccgta ggctgcagta aaaataagca acaagcttta tcatctgcaa    3660
cttttctttt tcatatcctc ttaataaggt ttaataacaa aaaattagag tatatacctt    3720
tagtcccgca caacctacta ttccggtaac aacggttaca gcttcaggat gtcgggcaac    3780
ctgttgatga acataataag taaaaaccta tctacactac aatcaaaact aacaaatgaa    3840
ctaacctcaa tcactccttg ctctcctgga ataatctcga gttatagtc caatcagct      3900 aaagcctctt taagctcatt aatcagtgac tcgtttctaa cagcaaccaa tgcaggctta    3960
aatctcctta cctgccacca ttcaaaatag aatcacagaa ccatactata gagatttctt    4020
gagattgcag aagcaaaagc ctaaaccaga acctgatttc tctggtttga tctgatacat    4080
aacgagttaa tactatcttg cttatgatac taccactgaa ctgagaatta aactgaattc    4140
caagtggtct gaatgacaaa ttggagagac tcaatactaa ttttttttaca aatgaagcca    4200
```

```
acttacctga tcagcaagta gagtaacatt cgaaccagca gctagagcca caactctgaa    4260
tttgtcagga ttctcagcca caatatccaa tgtctgcaaa atggaagttc ttgtcgataa    4320
aaatgatgca acaataactc agtaagaaaa aaatatcatt cttctatgag tctagtcatt    4380
cataagacaa acttaaagtc tggtcatact caagaactgc acaataatgc cttaatcgaa    4440
ataaaacctg agtgccaata gaaccagtag atccaacgat agagatgggt tttggtccat    4500
cccaagattg acgaggcgcc tcagggacag ctctcccagg ccatgctgga ggaggttgtt    4560
gttgctgctg cactttcact gaacacttaa caccttttcc aaaacctctc ccttgattcc    4620
tcctcctcaa actaaaccca cctgtgaaac actccaaaga tgtaaaattt aaaactctac    4680
gacctaaagc aaaccaaaaa aaatcgaatt gaagaaataa cagattaccT agatagagaa    4740
attcacaaga gcctaagaca actaatgaaa gtttgcaact ttaatcgaaa agagagttga    4800
ccaaggagga ggaaagaaga gaggaagaag aagaaacctg agagtttagg gattggattg    4860
aacctggagg tatccaagaa agaaatagct ttggattcag ctggagatag tgagtttaat    4920
gtcatcatca gagtctttta aaaatcgaat attttccaga gaaccgcact actactcttg    4980
attatcagag aagacgaatc agataaacag tgtgagagag agagatgatg ataagaaagg    5040
aatctggatt tgaatggtac ccaacagatt tttgtcattt tttaaagatt tcgctgagca    5100
tttagtaaca aggacctttt tattaaggta acgacaactg gtaagtggta aataatccag    5160
tcttactatg ttcccatttt ctatttgatt tctttagagt attaaacagc agaatctgta    5220
tcatcaatta tatagtttgt caaatataat tattattaga aatatgcatt acaagggatt    5280
aatggttaag gatttctctc ttacaaaata aaaagaaaa agtttatggt attcgttcgt    5340
attatgaatt tttgatatga atatcttaaa ttgaatatgt tttgactaac atgttgtatg    5400
ctgtcttttt caaaaataaa acatgttaca tgttttttttt ttcttcttct ctttttttt    5460 tttttttata agtacatgt tatatgctgt aacaattata atccaaatgt caaacttagt    5520
ttagatcttt gacaagtata taatatactt ttcttttaa aaattatgta ttgaatattt    5580
ttcactatca ttctttttt tttgtcaaca tttttcacta tcattcttat ttctttgata    5640
tgttcctcaa tgttcaattt gtaaatttaa atttcaaaag ccatgtaact ttaaccaact    5700
tgaatttttt acgtatataa ttctctatat ctctaattag agtcatgtta ggttcgattg    5760
tttaaataaa attagtcttc ttgtagacta ttagatcatc cgttcaaaaa gattattgtt    5820
gtttgaatgg tgctctcttt tctttcttcg gaaaggaata aaatttatcc cataaaagaa    5880
aaagaaaaag aaaaaagata atttacttta tttaagtgtg attaagctgt tatgattgac    5940
tatcacatta catagtgttt tcgtggggat acagagatca atagataaat gataatggta    6000
agataatggt atgttggtat tggtagatga gtcagtaaat catttactac tgctaatgga    6060
tcatctgagg acaagtgttg tacgttaagt gacacatggc aaaacagtga agagacgtt    6120 aaacaagtgt tacttgctgc atccactcaa attccatccc aagtcatgca tgcaacttt    6180 tctttaaaca tcggaaatcg gagcctgaat taatgcgtta actaatgaa acaaaaacca    6240 taattacggt gtagccatct ctccaattcc gattccattt caagttaacc ttatcgatat    6300
ggaggatagc aactctcacc cgcaaaatca aacatcaaaa agaaaagct ctcacccgca    6360 aaagaagcaa cgtatggaga atgaaacacg atcggctaag ttgttggatc ttgatgttct    6420
tgactgtccg gtttgcttcg agccgctcac tattcctacc tttcaggtta tgttttgaac    6480
ttgcatgcat tttattttgt ttcatgtgac attttgattt cgcttttgtt aattttattt    6540
attgaatacg gctttgattg tatctcgttt ggtatattat gcgtttcagt gtgatgatgg    6600
```

-continued

```
acatatagtt tgcaattttt gctttgccaa agtgagtaac aagtgccctg gtcctgggtg    6660
tgatttaccc attggtaata agcgatgctt cgcaatggag agggttctcg aatcagcctt    6720
tgttccatgt caaatactg agtttggctg cacaaaaagt gtctcttatg aaaagtgtc     6780 aagtcacgaa aaggaatgca actactctca atgctcttgc cctaacctcg aatgcaatta    6840
cactggctca tataacatca tctacggtca ctttatgcgt cgccatcttt acaatagtac    6900
gatcgtttcc tccaaatggg gatattccac tgttgatgtt ctaataaaca tcaaagaaaa    6960
ggtttcagtt ctctgggaat ctcgtcagaa acttttgttt gtagttcagt gtttcaagga    7020
gcgacatggt gtttatgtta ctgttagacg catcgcacca cctgcttcag aattcaagaa    7080
gttctcgtat cgtctttcgt atagtatcga cggacataat gttacttacg aatcaccaga    7140
agtaaagagg cttcttgaag tgaattctca aatccctgat gacagtttca tgtttgtccc    7200
taactgttta ctgcatggtg aaatgttgga gttgaagctt ggcatcaaga agttgaaaca    7260
aacgtaacta gatctagttt ggtttggggt tacgaggcgt tctgttttgt tgtgtttgtt    7320
ttaattctct gtttaagaac ctttgtactt ttgtagtagc ccactcttga atttattgat    7380
gttgttgttt tgagttagtt gtataatcca aaagctttct ggtttggttc ccggttcggt    7440
tttgtacata gtaggatttt taataaagcc tgctaatgag gttcagcaag ttaccattgc    7500
tcaggaaact gttatggagg atcctccaac gtctctgttt aagaattcag taccaattcg    7560
agaggatcaa attcagaacg ctatcacaaa ttccattcgc taatcttaga attgggcata    7620
aattctggaa taatgggctc atttggtatt agcgtccata cacattgtag gcccaataaa    7680
ataatagacc aagaaaaaac taaaaaccgg acaacgccgt tatctcttct tcgtgtgacc    7740
accacacata catacatacc actcaccgta ccaaaaagat tagaccaaca aaaaaaaaa     7800 aaaaaggacc agctcagatg agtctggagt ttccaagttt aaaacctctc tacctcgatt    7860
tgagcaaatc ctgatttact ctcatcctca tcatctctca tcatcgagat tcatagtctc    7920
ttttgccgct tggattcttc caaggttagt gagctgctat ggcaactcat cagcaaacgc    7980
aacctccttc cgattttccc gctcttgccg atgaaaattc ccagattcca ggttcaattt    8040
acaccttcta                                                          8050
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: conserved motif
<221> NAME/KEY: PEPTIDE
<222> LOCATION: (1)..(7)
<223> OTHER INFORMATION: Conserved amino acid sequence motif at N terminus of deoxyxylulose phosphate reductoisomerase

<400> SEQUENCE: 12

Gly Ser Thr Gly Ser Ile Gly
 1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: conserved motif
<221> NAME/KEY: PEPTIDE
<222> LOCATION: (1)..(10)

```
-continued

<223> OTHER INFORMATION: Conserved amino acid motif located at N
      terminus of ketol acid reductoisomerase wherein Xaa represents
      any amino acid

<400> SEQUENCE: 13

Gly Xaa Gly Xaa Xaa Gly Xaa Xaa Xaa Gly
 1               5                  10
```